(12) United States Patent
Sato et al.

(10) Patent No.: US 7,550,512 B2
(45) Date of Patent: Jun. 23, 2009

(54) MEDICAL POLYMERS AND USES THEREOF

(75) Inventors: Toshinori Sato, Yokohama-shi (JP); Yoshiyuki Koyama, Tokyo (JP); Tetsuji Yamaoka, Ibaraki-shi (JP)

(73) Assignees: Keio University, Tokyo (JP); NOF Corporation, Tokyo (JP)

( * ) Notice: Subject to any disclaimer, the term of this patent is extended or adjusted under 35 U.S.C. 154(b) by 898 days.

(21) Appl. No.: 10/859,598

(22) Filed: Jun. 3, 2004

(65) Prior Publication Data

US 2005/0036973 A1  Feb. 17, 2005

Related U.S. Application Data

(63) Continuation-in-part of application No. 10/469,136, filed as application No. PCT/JP02/12420 on Nov. 28, 2002, now abandoned.

(30) Foreign Application Priority Data

Nov. 28, 2001 (JP) ............................. 2001-362482
Nov. 27, 2002 (JP) ............................. 2002-343256

(51) Int. Cl.
*A61K 47/34* (2006.01)
*A61K 47/30* (2006.01)
*C08G 65/329* (2006.01)

(52) U.S. Cl. ............... 514/772.7; 424/70.13; 525/326.1
(58) Field of Classification Search ............. 514/772.4, 514/772; 424/70.13; 525/326.1
See application file for complete search history.

(56) References Cited

FOREIGN PATENT DOCUMENTS

| JP | 8048763 | 2/1996 |
|---|---|---|
| JP | 8048764 | 2/1996 |
| JP | 8291217 | 11/1996 |
| JP | 2000157270 | 6/2000 |
| WO | WO 01/26692 A1 | 4/2001 |

OTHER PUBLICATIONS

Koyama, Yoshiyuki, et al., "Sugar-Containing Polyanions as a Self-Assembled Coating of Plasmid/Polycation Complexes for Receptor-Mediated Gene Delivery," Macromol. Biosci., 2002, 2, 251-256.

*Primary Examiner*—Sharmila Gollamudi Landau
*Assistant Examiner*—Rachael E Welter
(74) *Attorney, Agent, or Firm*—Oblon, Spivak, McClelland, Maier & Neustadt, P.C.

(57) ABSTRACT

The present invention provides a polyethylene glycol derivative having sugar residue-containing side chains and carboxyl group-containing side chains, and a method of preparing the same. The present invention also provides a carrier for drug delivery systems and a carrier for gene transfer, both comprising the polyethylene glycol derivative.

3 Claims, 16 Drawing Sheets

MEDICAL POLYMERS AND USES THEREOF

CROSS-REFERENCE TO RELATED APPLICATION

This application is a Continuation-in-part application of U.S. application Ser. No. 10/469,136, pending.

BACKGROUND OF THE INVENTION

The present invention relates to medical polymers and uses thereof. More specifically, the present invention relates to polyethylene glycol derivatives having sugar residue-containing side chains and carboxyl group containing side chains, and their uses as a transporter for drugs or genes.

Drug delivery system is a therapeutic technology that controls the in vivo kinetics of drugs, delivers drugs selectively to targeted sites of action in the body, and thus realizes the optimization of therapeutic effect. Recently, studies of drug delivery systems have progressed rapidly. A great number of pharmaceutical formulations utilizing the drug delivery system technology have been commercialized, and administration methods developed by utilizing this technology have been gradually used in clinical scenes.

As drugs to be delivered by drug delivery systems, a wide range of pharmaceuticals such as anticancer drugs, drugs for the circulation system, or anti-inflammatory drugs have been studied. In these days, it is believed that drug delivery system is a technology indispensable in putting protein drugs into practical use and in realizing gene therapy.

At present, there are roughly two types of gene therapy methods actually practiced. One is a therapy method in which deficient genes in congenital genetic diseases (such as congenital immunodeficiency, inborn errors of metabolism, etc.) are complemented by introducing corresponding genes from outside. The other is a therapy method in which genes targeted to specific cells or viruses (such as cancer cells or AIDS virus) are introduced in order to inhibit propagation of or kill such cells or viruses. In both therapy methods, it is known that the important thing is to transfer a gene of interest into cells and to allow expression.

However, since DNA and cell membranes are both anionic and thus repel each other electrically, it is extremely difficult to introduce genes (DNA) alone directly into cells.

Under the circumstances, various materials have been examined as DNA carriers. However, they have problems with safety or transfer efficiency, which have prevented them from being used as DNA carriers. For example, retrovirus vectors, which are typical viral vector, have an advantage of high transfer efficiency, but have the following disadvantages: (1) they cannot transfer large size DNAs; (2) they cannot transfer DNA into non-dividing cells; and (3) the expression levels of DNAs transferred by them are low. Although adenovirus vectors are capable of transferring DNAs into non-dividing cells, they have a disadvantage of strong immunogenicity that leads to production of antibodies. Although herpesvirus vectors are excellent in DNA transfer into neurons, they have a disadvantage of strong cytotoxicity. With respect to carriers other than viral vectors, cationic liposomes, lipids, polymers, etc. have been studied. However, these materials have shown problems of low transfer efficiency or low cell specificity.

Japanese Unexamined Patent Publication No. 3-198782 discloses a method of gene transfer using a low molecular weight chitosan as a carrier. This method uses a drug that enhances the permeability of cell membranes when a gene of interest is transferred into cells. Thus, this method has a problem that cells are damaged.

The present inventors have solved the above-described problems by using a high molecular chitosan, and developed a carrier for gene transfer that can achieve a high expression level of the transferred gene and which yet is excellent in safety (Japanese Unexamined Patent Publication No. 2000-157270).

However, even in the case of using a high molecular weight chitosan as a carrier for gene transfer, there still remained problems that gene-chitosan complexes tend to aggregate and that the expression levels of genes are insufficient for therapeutic purposes.

It is an object of the present invention to provide materials that can be used as carriers for drug delivery systems and a method for preparing such materials.

It is another object of the present invention to provide carriers for drug delivery systems.

It is still another object of the present invention to provide drug delivery formulations.

Further, it is still another object of the present invention to provide carriers for gene transfer.

SUMMARY OF THE INVENTION

The present inventors synthesized polyethylene glycol derivatives having sugar residue-containing side chains and carboxyl group-containing side chains, coated complexes of a gene and a cationic polymer with the resultant polyethylene glycol derivative and administered the thus coated complexes into living bodies. As a result, the inventors have succeeded in achieving higher gene expression compared to cases where gene-cationic polymer complexes are used without such coating; thus, the present invention has been completed.

The first invention of the present application provides a copolymer, or a salt thereof, with a molecular weight of 1,000-200,000 comprising structural units represented by the general formulas (I), (II) and (III) described below.

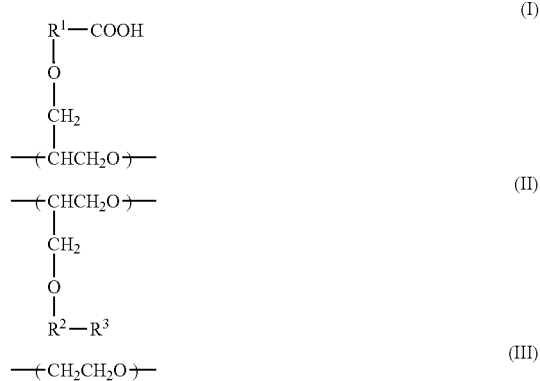

(where $R^1$ in general formula (I) and $R^2$ in general formula (II) are spacer moieties; $R^3$ in general formula (II) is a sugar residue; and the respective mole percents of units (I), (II) and (III) are (I)=1-98, (II)=1-98 and (III)=1-98.)

$R^1$ and $R^2$ are spacer moieties, and these spacer moieties may have a carboxyl group, a sugar residue and the like. The sugar of the sugar residue may be galactose, maltose, glucose, N-acetylglucosamine, N-acetylgalactosamine, fucose, sialic acid, mannose, lactose, cellobiose, maltotriose or the like.

R¹ may be a group represented by, for example, general formula (C) or (D) described below.

R² may be a group represented by, for example, general formula (B), (D) or (E) described below.

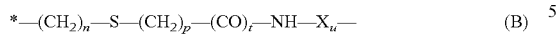 (B)

(where X is hydrocarbon group, n is an integer from 2 to 8; p is an integer from 1 to 8; t is an integer 0 or 1; and u is an integer 0 or 1.)

The hydrocarbon group of X may be aliphatic hydrocarbon group (e.g., alkylene group having 1 to 8 carbon atoms), aromatic hydrocarbon group (e.g., phenylen group, naphthylene group) or the like, preferably, is alkylene group having 2 to 5 carbon atoms, phenylene group or the like, more preferably, is alkylene group having 2 to 5 carbon atoms.

 (C)

(where m is an integer from 2 to 8; and p is an integer from 1 to 8.)

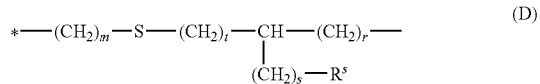 (D)

(where m is an integer from 2 to 8; r is an integer from 0 to 7; s is an integer from 0 to 7; t is an integer from 0 to 4: and $R^s$ is an amino group, carboxyl group or sugar residue.)

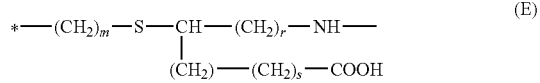 (E)

(where m is an integer from 2 to 8; r is an integer from 0 to 7; and s is an integer from 0 to 7.)

(where m is an integer from 2 to 8; r is an integer from 0 to 7; s is an integer from 0 to 7.)

In general formulas (B), (C), (D) and (E), * may be positioned on the ethylene oxide side or on the opposite side (in R¹ on the carboxyl group side, and in R² on R³ side). Preferably, * is positioned on the ethylene oxide side.

Specific examples of the group represented by general formula (B) include:

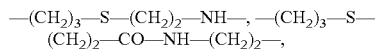

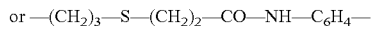

Specific examples of the group represented by general formula (C) include:

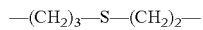

Specific examples of the group represented by general formula (D) include:

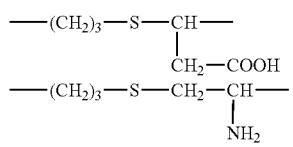

Specific examples of the group represented by general formula (E) include:

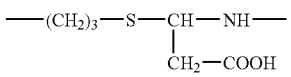

As R¹, the following groups are preferable from the viewpoint of synthesis.

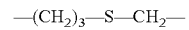

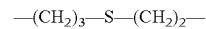

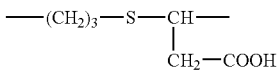

As R², the following groups are preferable from the viewpoint of synthesis.

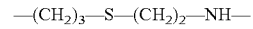

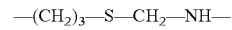

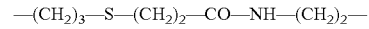

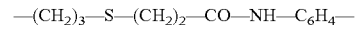

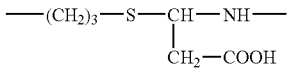

When $R^s$ in general formula (D) is a sugar residue, the sugar of the sugar residue may be galactose, maltose, glucose, N-acetylglucosamine, N-acetylgalactosamine, fucose, sialic acid, mannose, lactose, cellobiose, maltotriose or the like.

When R³ is a sugar residue, the sugar of the sugar residue may be galactose, maltose, glucose, N-acetylglucosamine, N-acetylgalactosamine, fucose, sialic acid, mannose, lactose, cellobiose, maltotriose or the like.

When R³ is a sugar residue, the sugar of the sugar residue also include sugar lactone such as lactonolactone, maltonolactone, gluconolactone, maltotrionolactone, cellobionolactone, galactonolactone, N-acetylglucosaminolactone, N-acetylgalactosaminolactone, sialolactone, mannolactone or the like.

The total sum of the mole percent of unit (I) and the mole percent of unit (II) in the copolymer of the first invention of the present application ranges preferably from 5 to 60 mole percent, and more preferably from 10 to 40 mole percent.

The respective mole percents of units (I), (II) and (III) in the copolymer of the first invention of the present application are preferably 3-58:2-57:40-95, more preferably 6-36:4-34: 60-90.

The copolymer of the first invention of the present application may further comprise other units, e.g., propylene oxide.

The copolymer of the first invention of the present application may be either a random copolymer, block copolymer or graft copolymer, more preferably, is a random copolymer.

Specific examples of the salts of the copolymer of the first invention of the present application include sodium salts and potassium salts.

The second invention of the present application provides a method of preparing a copolymer with a molecular weight of 1,000-200,000 having sugar residue-containing side chains and carboxyl group-containing side chains, comprising polymerizing a compound represented by the following general formula (IV):

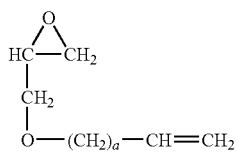
(IV)

(where a is an integer from 0 to 6.)
and ethylene oxide, adding to the resultant copolymer a mixture of a mercaptoalkylamine and a mercapto-fatty acid, reacting the mixture with the copolymer, thereby obtaining a copolymer having amino group-containing side chains and carboxyl group-containing side chains, and then reacting the resultant copolymer having amino group-containing side chains and carboxyl group-containing side chains with a sugar lactone.

As the compound represented by the general formula (IV), allylglycidyl ether is preferred.

The molar ratio of the compound represented by the general formula (IV) to ethylene oxide may be in the range from 1:99 to 70:30, preferably from 5:95 to 50:50, and more preferably from 10:90 to 40:60.

As the mercaptoalkylamine, a compound represented by the following general formula:

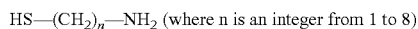
HS—(CH$_2$)$_n$—NH$_2$ (where n is an integer from 1 to 8)

may be used. Specifically, mercaptoethylamine may be given as an example.

As the mercapto-fatty acid, a compound represented by the following general formula:

HS—(CH$_2$)$_n$—COOH
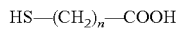

(where n is an integer from 1 to 8)
may be used. Specifically, mercaptoacetic acid, mercaptopropionic acid or the like may be enumerated.

The mixing molar ratio of a mercaptoalkylamine to a mercapto-fatty acid in the synthesis may be in the range from 1:99 to 70:30, preferably from 5:95 to 40:60, and more preferably from 15:85 to 30:70.

The molar ratio of the double bonds in the copolymer obtained by polymerizing a compound represented by the general formula (IV) and ethylene oxide to the mixture of a mercaptoalkylamine and a mercapto-fatty acid may be in the range from 1:1 to 1:80, preferably from 1:1.5 to 1:50, and more preferably from 1:2 to 1:30.

As the sugar lactone, lactonolactone, maltonolactone, gluconolactone, maltotrionolactone, cellobionolactone, galactonolactone, N-acetylglucosaminolactone, N-acetylgalactosaminolactone, sialolactone, mannolactone or the like may be enumerated.

The molar ratio of the amino groups in the copolymer having amino group-containing side chains and carboxyl group-containing side chains to the sugar lactone may be in the range from 1:1 to 1:20, preferably from 1:1.3 to 1:10, and more preferably from 1:1.5 to :15.

The molecular weight of a copolymer having sugar residue-containing side chains and carboxyl group-containing side chains as prepared by the above-described method is preferably 2,000-200,000, and more preferably 4,000-50,000.

According to the above-described method, a random copolymer, block copolymer and graft copolymer or a copolymer including combinations of these copolymers can be prepared, and the preparation of a random copolymer is preferred.

According to the method of the second invention of the present application, the copolymer of the first invention of the present application can be prepared.

The third invention of the present application provides a method of preparing a copolymer with a molecular weight of 1,000-200,000 having sugar residue-containing side chains and carboxyl group-containing side chains, comprising polymerizing a compound represented by the following general formula (IV):

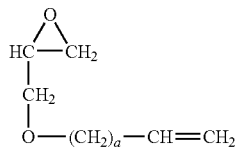
(IV)

(where a is an integer from 0 to 6.)
and ethylene oxide, adding to the resultant copolymer a mercapto-fatty acid, reacting the mercapto-fatty acid with the copolymer, thereby obtaining a copolymer having carboxyl group-containing side chains, and then reacting the resultant copolymer having carboxyl group-containing side chains with a sugar derivative having amino groups.

As the compound represented by the general formula (IV), allylglycidyl ether is preferred.

The molar ratio of the compound represented by the general formula (IV) to ethylene oxide may be in the range from 1:99 to 70:30, preferably from 5:95 to 50:50, and more preferably from 10:90 to 40:60.

As the mercapto-fatty acid, a compound represented by the following general formula:

HS—(CH$_2$)$_n$—COOH (where n is an integer from 1 to 8)
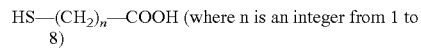

may be used. Specifically, mercaptoacetic acid, mercaptopropionic acid or the like may be enumerated.

The molar ratio of the double bonds in the copolymer obtained by polymerizing a compound represented by the general formula (IV) and ethylene oxide to the mercapto-fatty acid may be in the range from 1:1 to 1:80, preferably from 1:1.5 to 1:50, and more preferably from 1:2 to 1:30.

Specific examples of the sugar derivative having amino groups include, but are not limited to, hexoses in which an amino group is attached to the carbon atom at position 1 (e.g. 1-amino-1-deoxy-glucose, 1-amino-1-deoxy-galactose, 1-amino-1-deoxy-mannose, 1-amino-1-deoxy-glucitol, 1-amino-1-deoxy-galacitol, 1-amino-1-deoxy-mannocitol); hexoses in which an amino group is attached to the carbon atom at position 2 (e.g. 2-amino-2-deoxy-glucose, 2-amino-2-deoxy-galactose, 2-amino-2-deoxy-mannose); hexoses in which an amino group is attached to the carbon atom at position 6 (e.g. 6-amino-6-deoxy-glucose, 6-amino-6-deoxy-galactose, 6-amino-6-deoxy-mannose); hexoses in which p-aminophenol is attached to a hydroxyl group attached to the carbon atom at position 1 (e.g., p-aminophenyl-glucoside, p-aminophenyl-galactoside, p-aminophenyl-mannoside); and hexoses in which alkylamine (e.g. alkylamine having 1to 8 carbon atoms) is attached to a hydroxyl group attached to the carbon atom at position 1 (e.g., 2-aminoethylgalactopyranoside 2-aminoethylmannopyranoside).

The mixing molar ratio of the carboxyl groups in the copolymer having carboxyl group-containing side chains to the sugar derivative having amino groups may be in the range from 1:1 to 100:1, preferably from 3:2 to 50:1, and more preferably from 2:1 to 10:1.

The molecular weight of a copolymer having sugar residue-containing side chains and carboxyl group-containing side chains prepared by the above-described method is preferably 2,000-200,000, and more preferably 4,000-50,000.

According to the above-described method, a random copolymer, block copolymer and graft copolymer or a copolymer including of combinations of these copolymers can be prepared, and the preparation of random copolymer is preferred.

According to the method of the third invention of the present application, the copolymer of the first invention of the present application can be prepared.

The fourth invention of the present application provides a carrier for drug delivery systems comprising the copolymer, or a salt thereof, of the first invention of the present application.

The fifth invention of the present application provides a drug delivery formulation comprising a drug and the copolymer, or a salt thereof, of the first invention of the present application.

As the drug, a nucleic acid or nucleic acid derivative such as gene, anti-sense nucleic acid.or ribozyme, a polymeric immunopotentiator, cAMP, a medicament such as prostaglandin, daunomycin or the like may be enumerated.

The sixth invention of the present application provides a carrier for gene transfer comprising the copolymer, or a salt thereof, of the first invention of the present application.

The carrier for drug delivery systems and the carrier for gene transfer of the present invention as well as the drug delivery formulation of the present invention may further comprise a cationic polymer (hereinafter, referred to as a "polycation"). This polycation may be selected from the group consisting of high molecular weight chitosan (Biomaterials, Vol. 22, 2001, pp. 2075-2080; Biochim. Biophys. Acta. Vol. 1514, 2001, pp. 51-64), poly-L-lysine, polyamidoamine dendrimers, DEAE-dextran (for review of these polymers, see Nonviral Vectors for Gene Therapy, Academic Press, Inc., 1999), polyethyleneimine and combinations of these polymers.

Nucleic acids (or derivatives thereof) electrostatically bond with polycations, forming complexes folded into a small shape. Since these complexes are usually taken into cells by endocytosis, most part of the complexes is degraded by enzymes in endosomes that have become weakly acidic. On the other hand, the polyethylene derivative of the invention having sugar residue-containing side chains and carboxyl group-containing side chains is negatively charged, so it is believed to have a cell membrane disrupting function under weakly acidic conditions. By coating a nucleic acid-polycation complex with such an anionic polymer, it is believed that the anionic polymer disrupts endosome membranes before the nucleic acid is enzymatically degraded and allows the nucleic acid to migrate into the cytoplasm, to thereby improve gene expression efficiency. Further, the polyethylene derivative of the present invention is hydrophilic, so it is believed to prevent the aggregation of nucleic acid-polycation complexes caused by serum proteins.

The combining ratio of the nucleic acid (or a derivative thereof) to the polycation (molar ratio between individual charged groups; anion:cation ratio) may be in the range from 1:0.1 to 1:50, preferably from 1:1 to 1:20, and more preferably from 1:2 to 1:10.

The combining ratio of the polycation to the copolymer of the first invention of the present application (molar ratio between individual charged groups; cation:anion ratio) may be in the range from 1:0.01 to 1:20, preferably from 1:0.1 to 1:16, and more preferably from 1:0.2 to 1:10.

The copolymer of the first invention of the present application has a polyethylene glycol main chain, so it can be expected to inhibit aggregation or activation of complements, etc. in solutions or body fluids such as blood. Further, the copolymer has sugar residue-containing side chains, so it enables delivery of drugs specific to those cells which recognize the sugar chain (e.g. cancer cells). Moreover, the copolymer can be expected to improve water-solubility of formulations.

The seventh invention of the present application provides a carrier for gene transfer comprising an anionic polymer having pendant sugar residues or a salt thereof, and a cationic polymer. As the cationic polymer, chitosan is preferably used.

Specific examples of the anionic polymer having pendant sugar residues or salts thereof include the copolymer, or salts thereof, of the first invention of the present application, condensation products from carboxyvinyl polymers and amino group-containing sugar derivatives, and acidic mucopolysaccharides such as hyaluronic acid though not having sugar residues in side chains.

Specific examples of the cationic polymer include, in addition to chitosan, poly-L-lysine, polyamidoamine dentrimers, polyethyleneimine, protamine, DEAE-dextran and polylysine dendrimers.

The combining ratio of the cationic polymer to the anionic polymer having pendant sugar residues (molar ratio between charged groups contained in individual polymers; cation:anion ratio) may be in the range from 1:0.01 to 1:20, preferably from 1:0.1 to 1:16, and more preferably from 1:0.2 to 1:10.

The combining ratio of the nucleic acid (or a derivative thereof) to the polycation (molar ratio between individual charged groups; anion:cation ratio) may be in the range from 1:0.1 to 1:50, preferably from 1:1 to 1:20, and more preferably from 1:2 to 1:10.

The eighth invention of the present application provides a carrier for gene transfer comprising a copolymer, or a salt thereof, with a molecular weight of 1,000-200,000 containing structural units represented by the following general formulas (I) and (III), and chitosan.

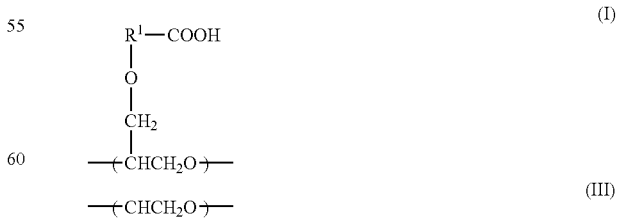

(where $R^1$ in general formula (I) is a spacer moiety; and the respective mole percents of structural units (I) and (III) are (I)=1-80 and (III)=20-99.)

R[1] is a spacer moiety, which may have a carboxyl group, sugar residue, or the like. The sugar of the sugar residue may be galactose, maltose, glucose, N-acetylglucosamine, N-acetylgalactosamine, fucose, sialic acid, mannose, lactose, cellobiose, maltotriose or the like.

R[1] may be a group represented by, for example, general formula (C) or (D) described below.

(C)

(where m is an integer from 2 to 8; and p is an integer from 1 to 8.)

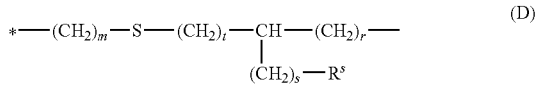
(D)

(where m is an integer from 2 to 8; r is an integer from 0 to 7; s is an integer from 0 to 7; t is an integer from 0 to 4: and R[s] is an amino group, carboxyl group or sugar residue.)

In general formulas (C) and (D), * may be positioned on the ethylene oxide side or on the opposite side (on the carboxyl group side). Preferably, * is positioned on the ethylene oxide side.

Specific examples of the group represented by general formula (C) include:

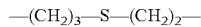

Specific examples of the group represented by general formula (D) include:

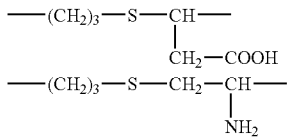

As R[1], the following groups are preferable from the viewpoint of synthesis.

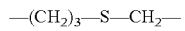

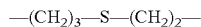

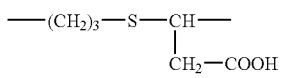

When R[s] in general formula (D) is a sugar residue, the sugar of the sugar residue may be galactose, maltose, glucose, N-acetylglucosamine, N-acetylgalactosamine, fucose, sialic acid, mannose, lactose, cellobiose, maltotriose or the like.

The respective mole percents of structural units (I) and (III) in the copolymer used in the eighth invention of the present application are preferably 1-80:99-20, and more preferably 3-60:97-40.

The copolymer used in the eighth invention of the present application may further comprise other units such as propylene oxide.

The copolymer used in the eighth invention of the present application may be either a random copolymer, block copolymer or graft copolymer, more preferably, is a random copolymer.

The copolymer used in the eighth invention of the present application can be prepared by polymerizing a compound represented by the following general formula (IV):

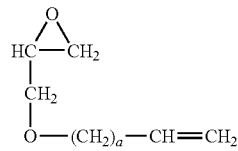
(IV)

(where a is an integer from 0 to 6.)

and ethylene oxide and adding to the resultant copolymer a mercapto-fatty acid to react the mercapto-fatty acid with the copolymer. A compound represented by the general formula (IV) and polymerization thereof, and a mercapto-fatty acid and reaction thereof are as described in the explanation of the third invention of the present application.

Specific examples of the salt of the copolymer used in the eighth invention of the present application include sodium salts and potassium salts.

In the carrier for gene transfer of the eighth invention of the present application, the combination ratio of chitosan to the copolymer or salt thereof (molar ratio between individual charged groups; cation:anion ratio) may be in the range from 1:0.01 to 1:20, preferably from 1:0.1 to :1:16, and more preferably from 1:0.2 to 1:10.

The combination ratio of the nucleic acid (or derivative thereof) to the polycation (molar ratio between individual charged groups; anion:cation ratio) may be in the range from 1:0.1 to 1:50, preferably from 1:1 to 1:20, and more preferably from 1:2 to 1:10.

The present specification includes the contents of the specifications and/or drawings of Japanese Patent Applications (i.e., Japanese Patent Applications Nos. 2001-362482 and 2002-343256) and PCT Application (i.e., PCT/JP02/12420) based on which the present application claims priority.

The spectrum of the H indicated with an open star mark partly overlaps with the spectrum of the underlined H in the —CH(OH)— of the sugar residue.

Figure 7:
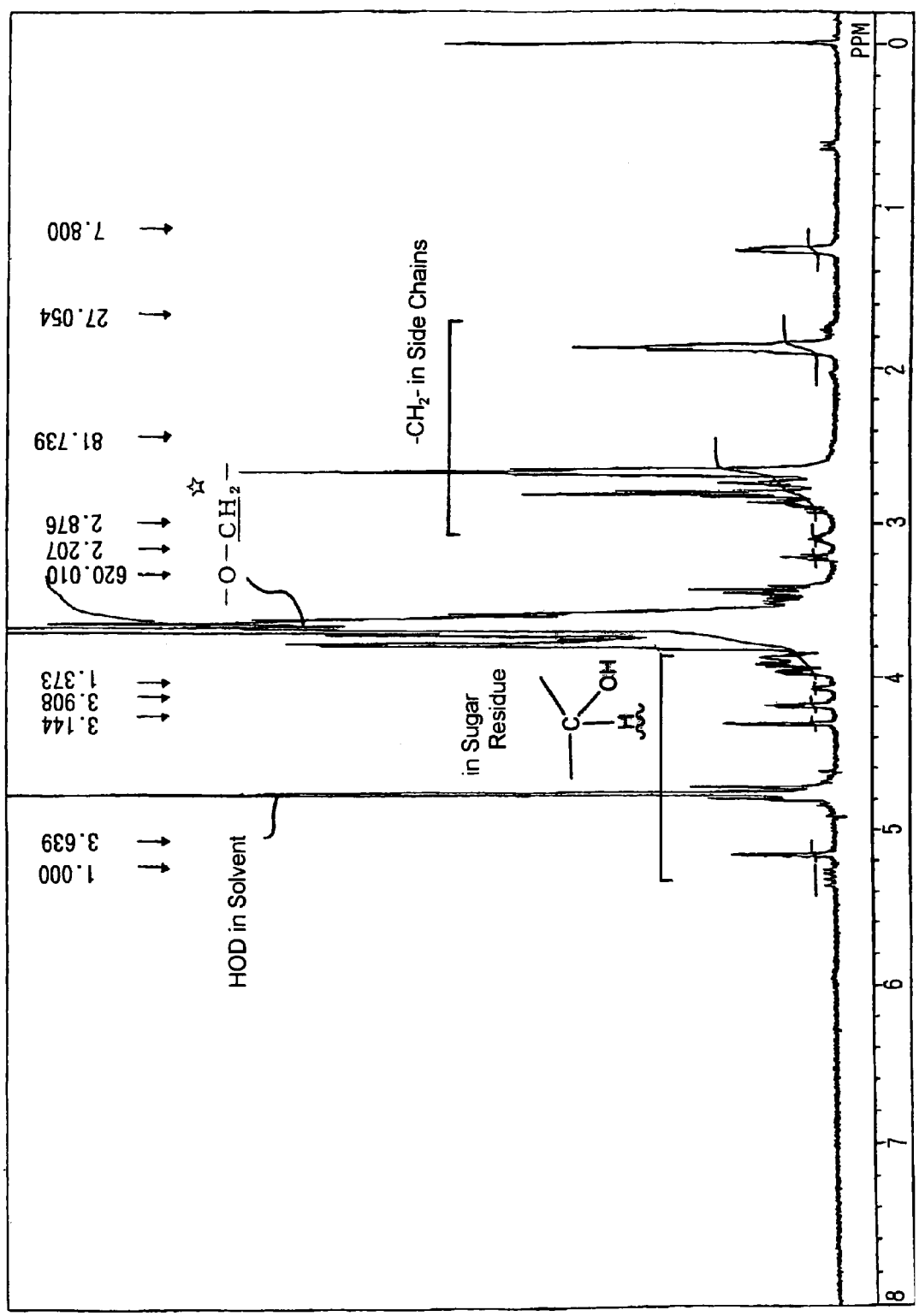

FIG. 7 is an NMR spectrum of Mal-PEG-A/C.

The spectrum of the H indicated with an open star mark partly overlaps with the spectrum of the underlined H in the —CH(OH)— of the sugar residue.

Figure 8:
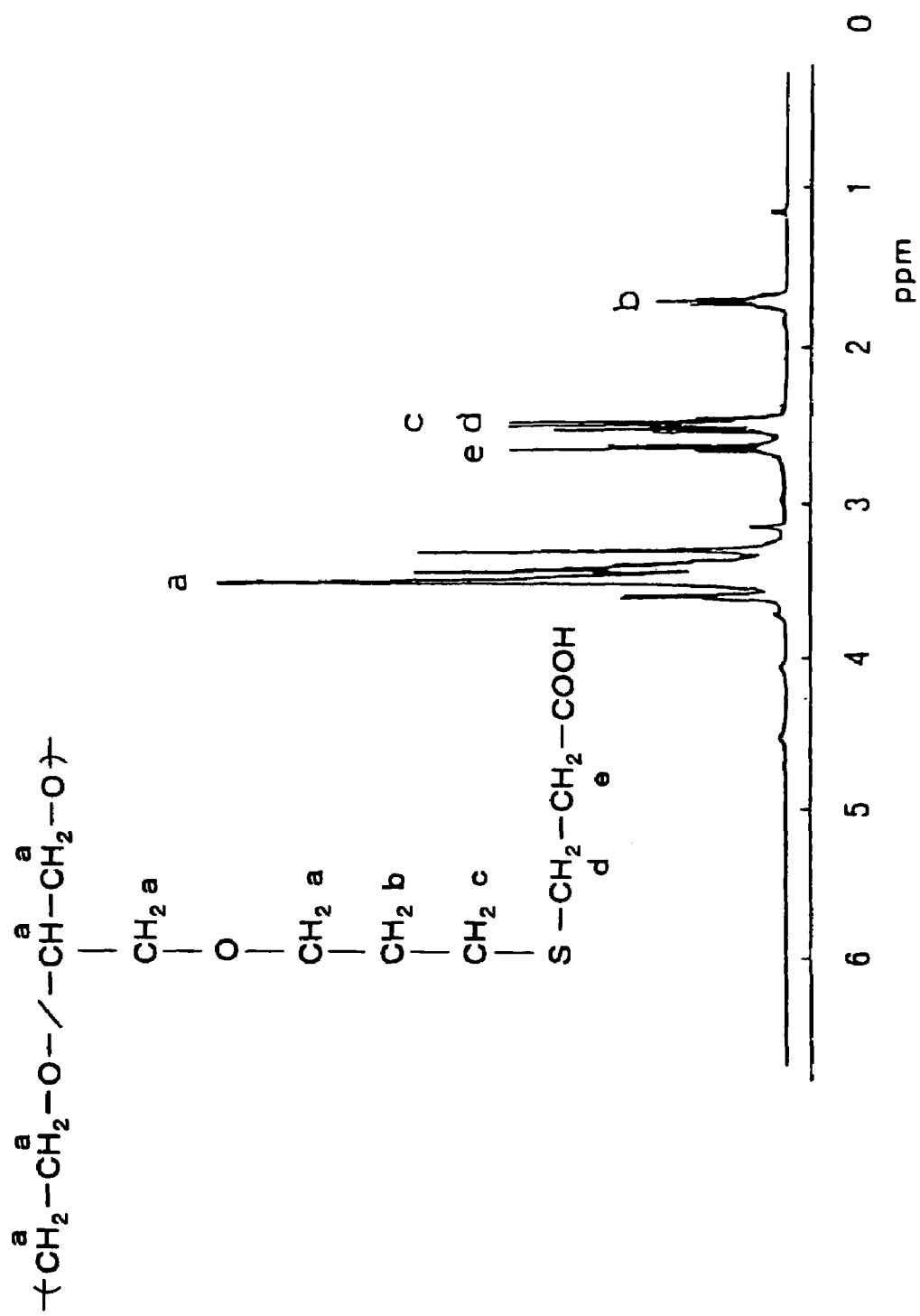

FIG. 8 is an NMR spectrum of PEG-C9000.

Figure 9:
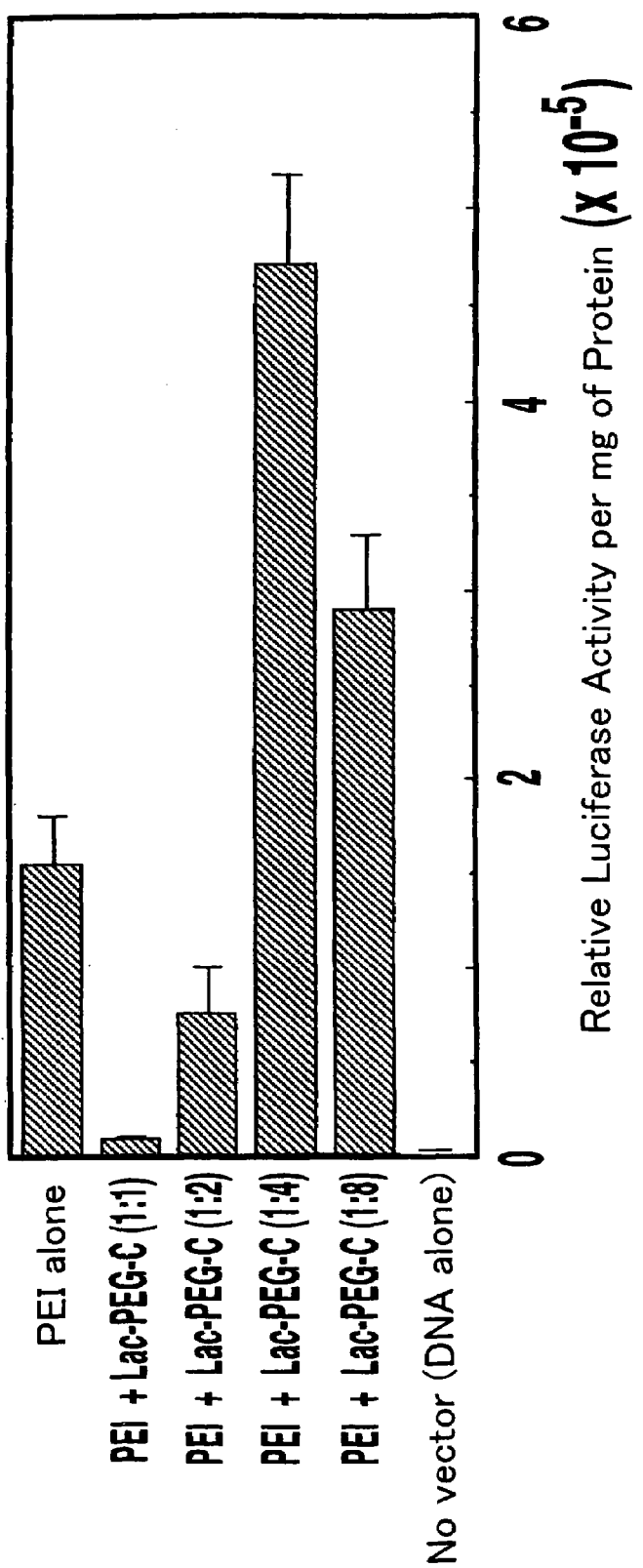

FIG. 9 is a graph showing the effect of anion/cation ratios in Lac-PEG-A/C.

Figure 10:
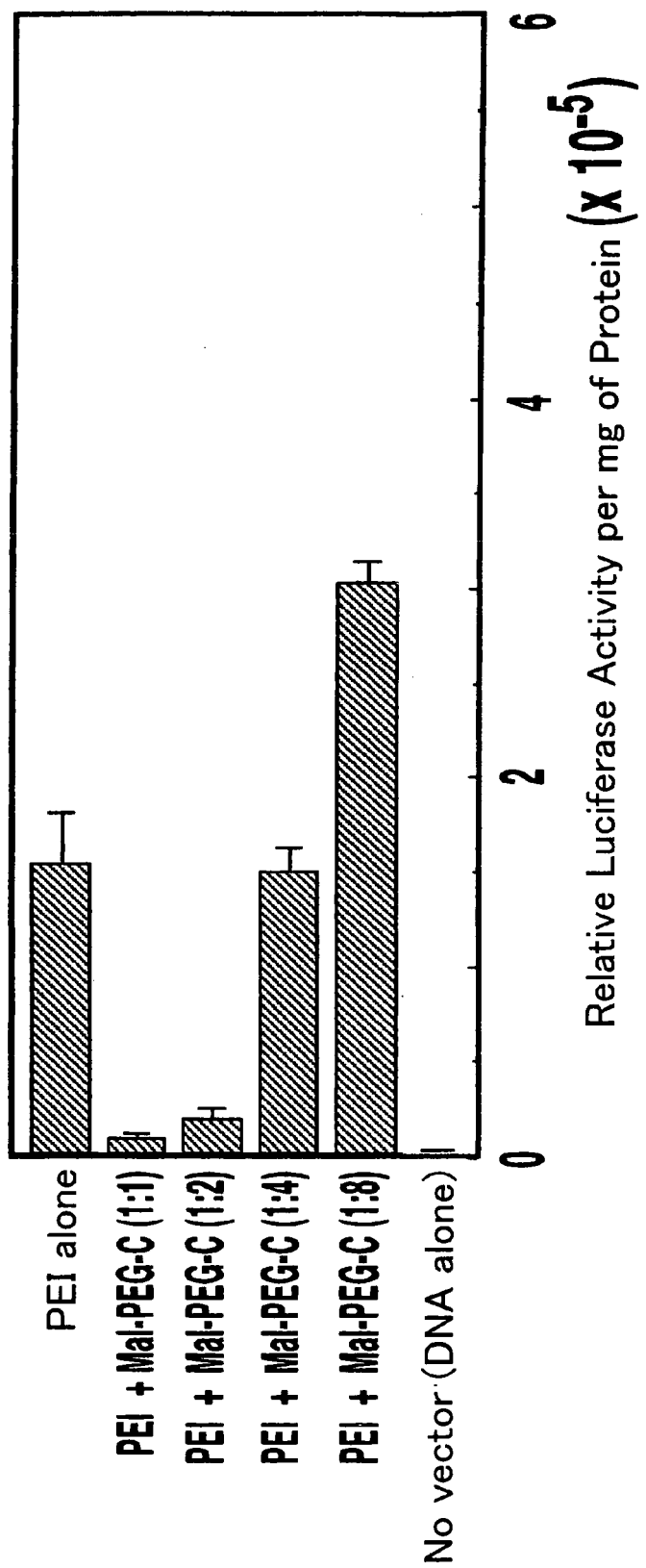

FIG. 10 is a graph showing the effect of anion/cation ratios in Mal-PEG-A/C.

Figure 11:
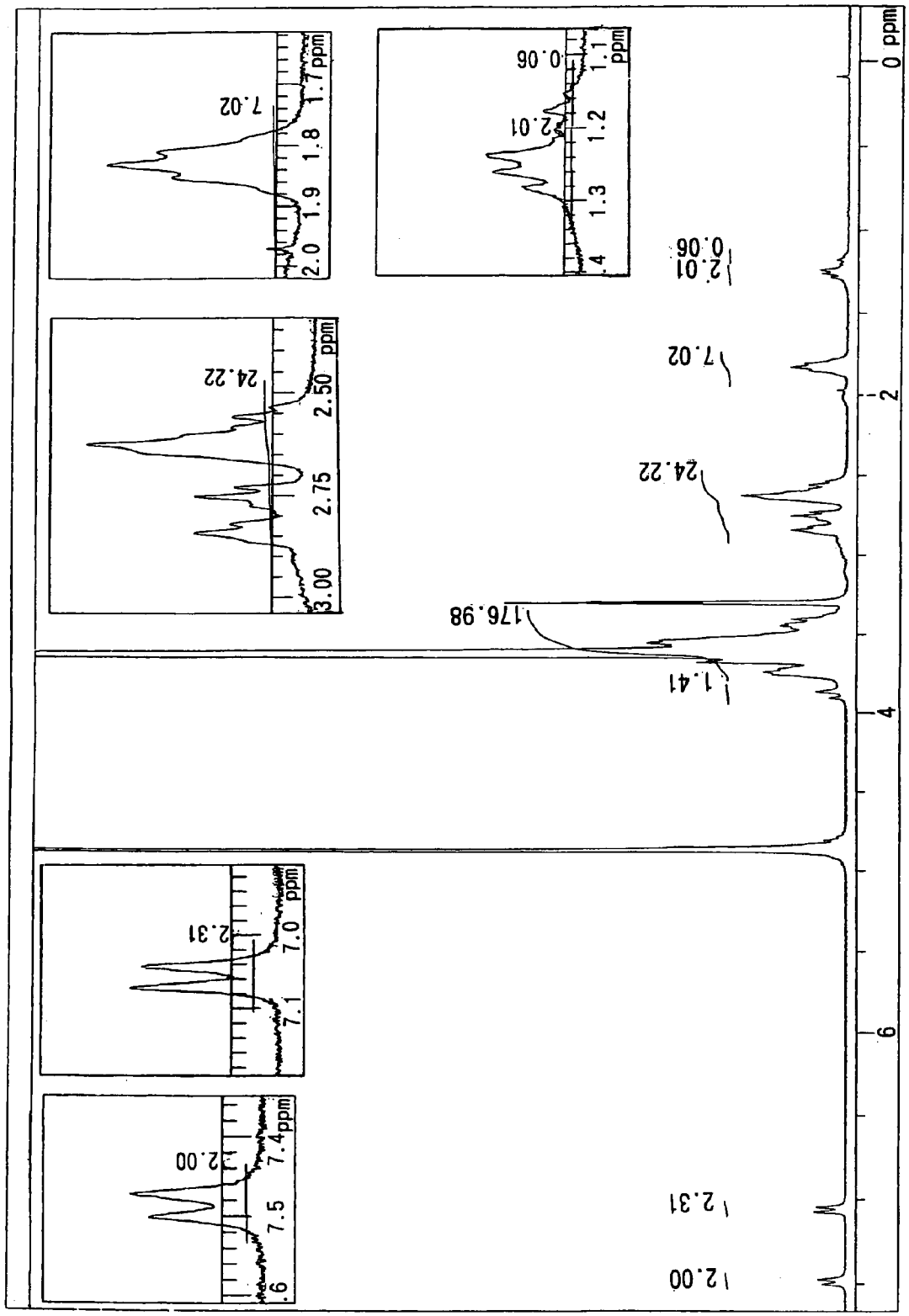

FIG. 11 is an NMR spectrum of Gul-N-PEG-C.

Figure 12:
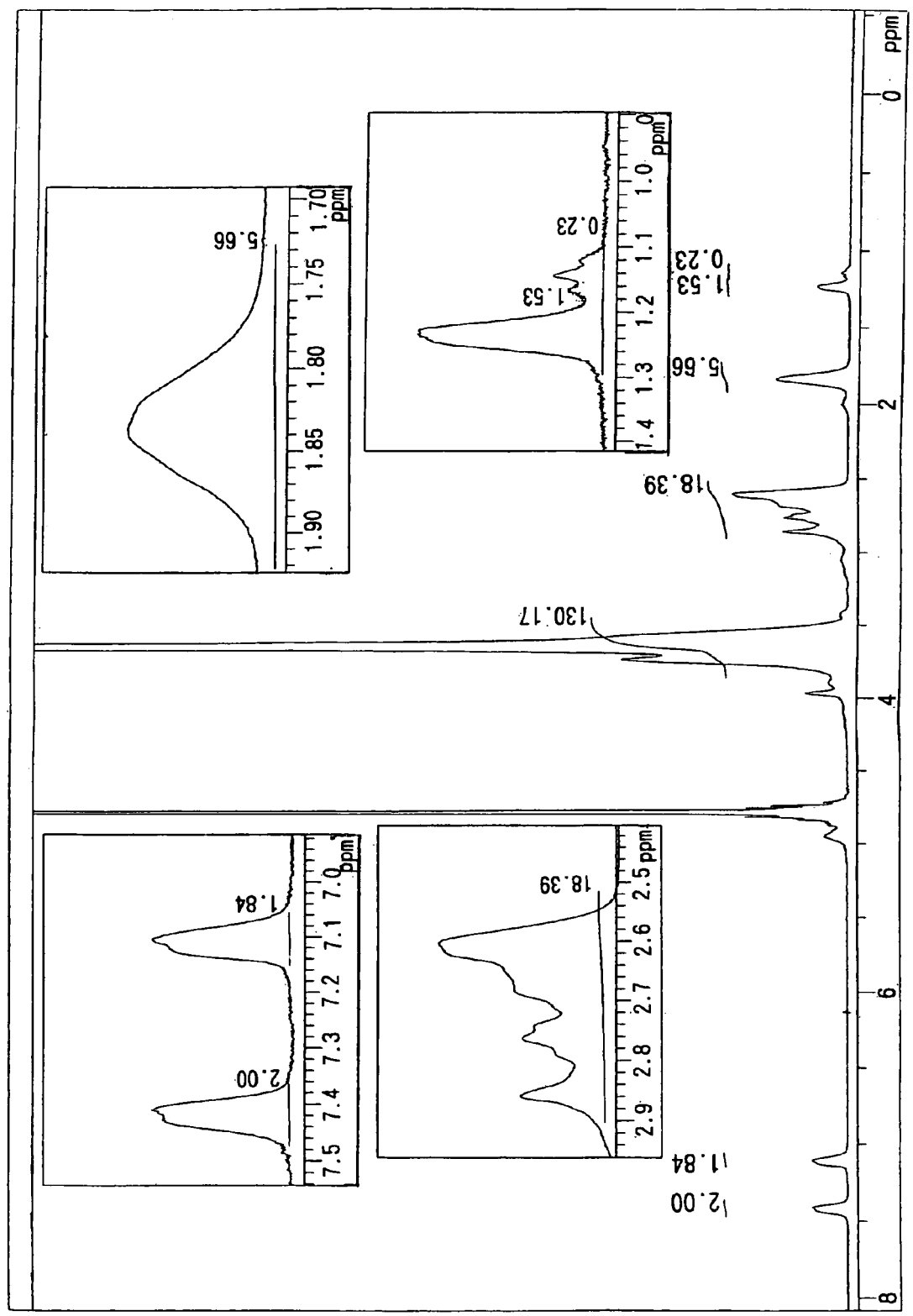

FIG. 12 is an NMR spectrum of Gal-N-PEG-C.

Figure 13:
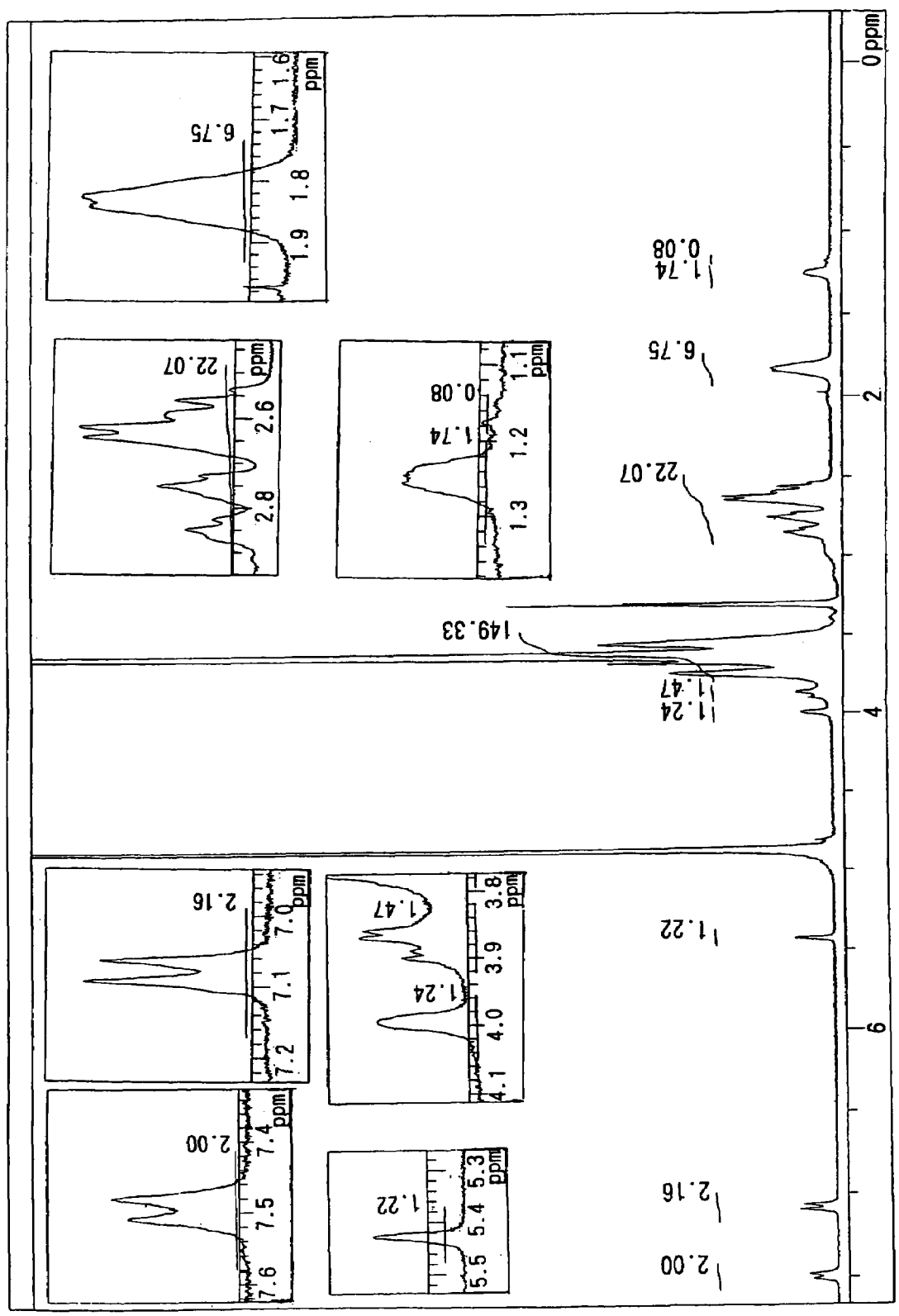

FIG. 13 is an NMR spectrum of Man-N-PEG-C.

Figure 14:
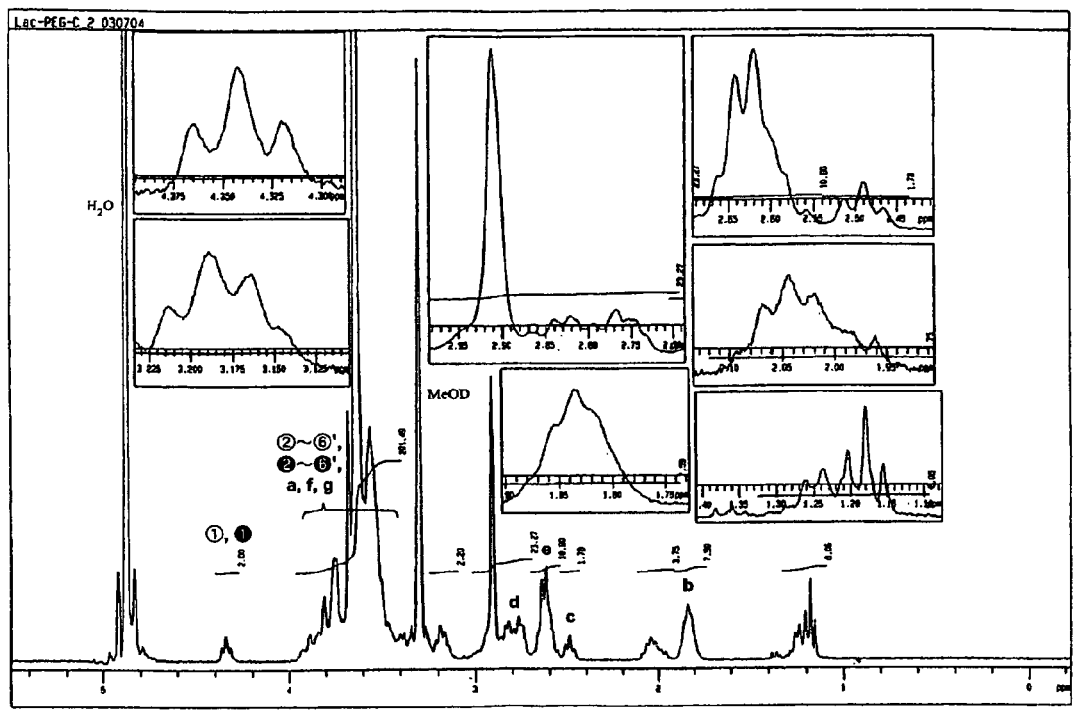
Figure 14:
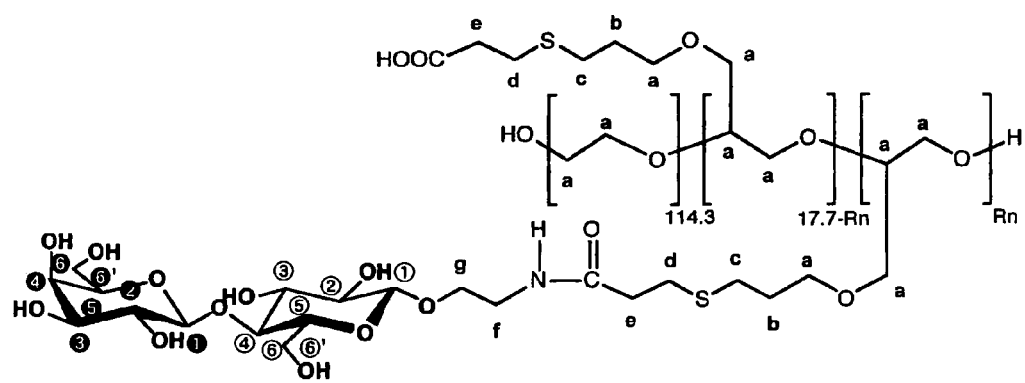

FIG. 14 is an NMR spectrum of Lac-$C_2H_4$—$NH_2$.

Figure 15:
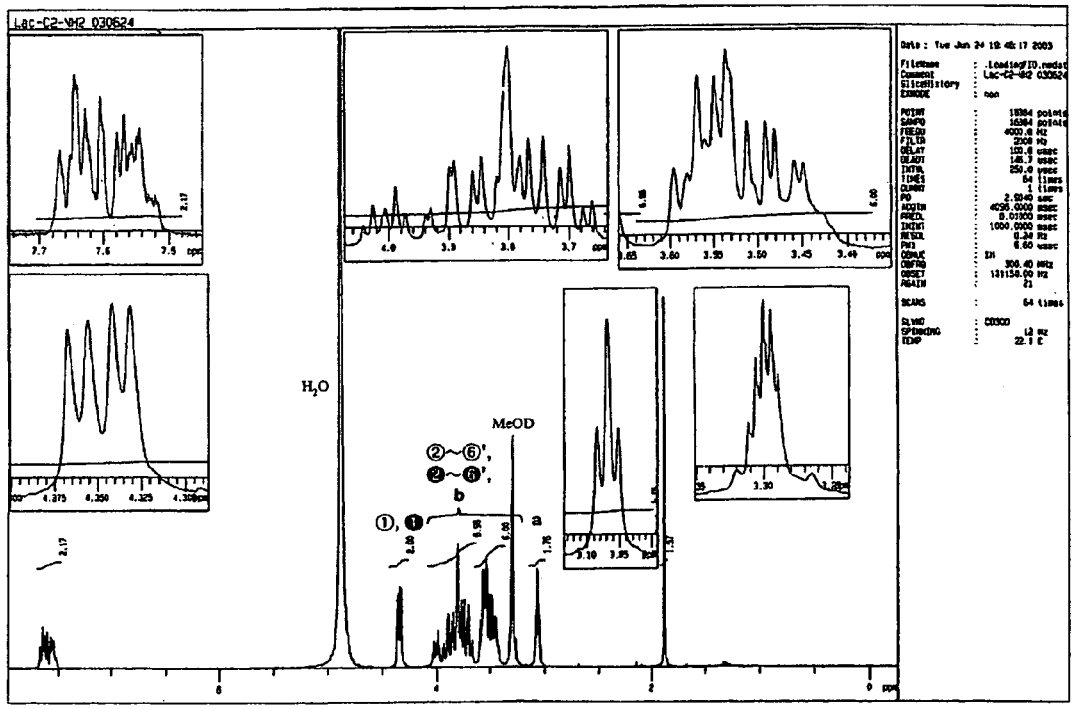
Figure 15:
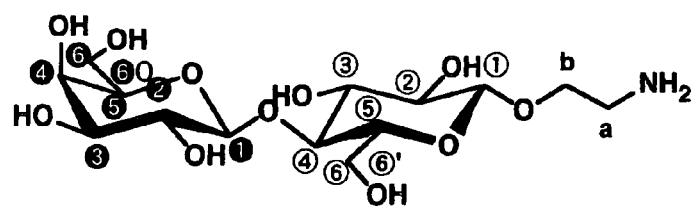

FIG. 15 is an NMR spectrum of Lac-PEG-C.

Figure 16:
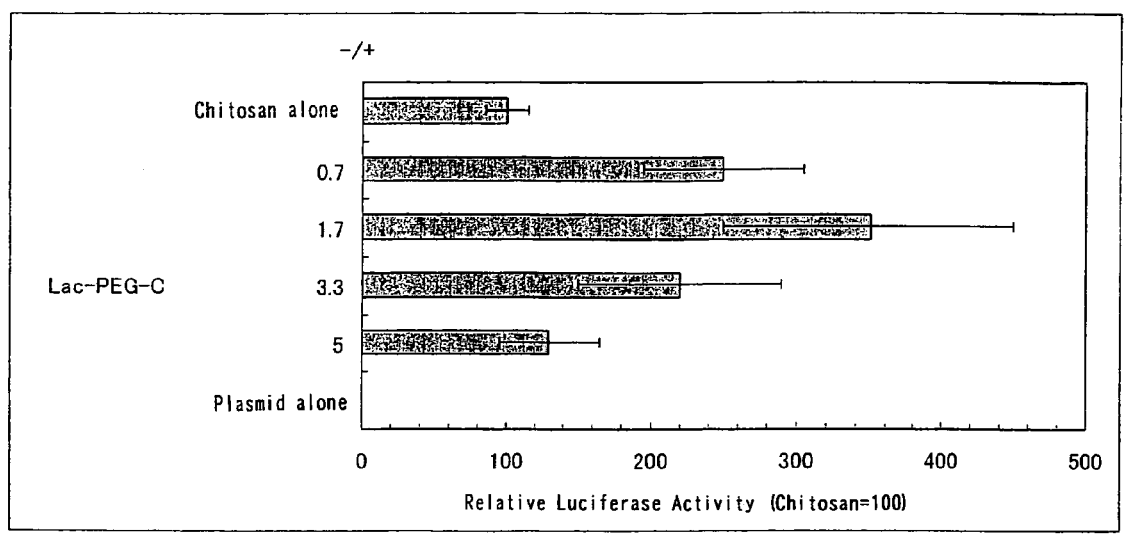

FIG. 16 is a graph showing the effect of anion/cation ratios in Lac-PEG-C.

DESCRIPTION OF THE PREFERRED EMBODIMENT

Hereinbelow, one of the preferred embodiments of the present invention is described.

1. Preparation of Polyethylene Glycol Derivatives 1-1 Preparation of Copolymers Having Sugar Residue-Containing Side Chains and Carboxyl Group-Containing Side Chains (1st Method)

(1) Preparation of Copolymers of Allylglycidyl Ether and Ethylene Oxide

Diethylene glycol and potassium hydroxide are placed in a reactor (the molar ratio of diethylene glycol to potassium hydroxide may be preferably from 1:0.3 to 1:1) and dehydrated under a nitrogen atmosphere at about 20-70 mmHg for 0.5-3 hr at 70-95° C. Then, a mixture of allylglycidyl ether (AGE) and ethylene oxide (EO) (molar ratio: from 1:99 to 70:30) is added dropwise at 100-120° C. at a rate of about 50-600 g/h. The molecular weight of the resulting polymer is controlled by the amounts of monomers added. immediately after the addition of the monomers, unreacted monomers are removed under reduced pressure (e.g. 200 mmHg). After neutralization with phosphoric acid, the resultant polymer is dehydrated at 80-120° C. for 0.5-3 hr under reduced pressure, followed by filtration at 60-95° C.

The molecular weight of the copolymer of allylglycidyl ether and ethylene oxide can be determined by the hydroxyl titration method (JIS K-1557 6.4 (1970)). The polymer composition can be determined by the double-bond titration method (JIS K-1557 6.7 (1970)). The molecular weight distribution can be examined by GPC (solvent: THF).

The copolymer obtained by the above-described method is a random copolymer. If a copolymer in which the two monomers are highly grouped is desired, a monomer mixture should be added at once; and if a block copolymer is desired, individual monomers should be added separately in consecutive order.

(2) Preparation of PEG Derivatives having Both Pendant Amino Groups and Pendant Carboxyl Groups (PEG-A/C)

The copolymer of allylglycidyl ether and ethylene oxide obtained in (1) above is dissolved in methanol, added dropwise with stirring to a mixture of mercaptoalkylamine and a mercapto-fatty acid pre-dissolved in methanol, and reacted at 20-60° C. for 8-72 hr. After dialysis against flowing water for 1-4 days and against pure water for 0-2 days, the reaction mixture is lyophilized, or the solvent is removed under reduced pressured from the reaction mixture, to thereby obtain a PEG derivative having both pendant amino groups and pendant carboxyl groups (PEG-A/C). The mixing molar ratio of the mercaptoalkylamine to the mercapto-fatty acid in the reaction may be in the range from 1:99 to 70:30.

The molecular weight of the resultant PEG-A/C can be calculated based on the molecular weight of the copolymer of allylglycidyl ether and ethylene oxide from (1) above by determining the numbers of amino group-containing side chains and carboxyl group-containing side chains by suitable techniques such as NMR. Briefly, the molecular weight of PEG-A/C can be calculated by adding up the following: [the molecular weight of the copolymer of allylglycidyl ether and ethylene oxide], [the product of the molecular weight of the added mercaptoalkylamine and the number of molecules added] and [the product of the molecular weight of the added mercapto-fatty acid and the number of the molecules added]. This calculation is made on the assumption that the reaction ratio was 100%.

(3) Preparation of Polyethylene Glycol Derivatives having Sugar Residue-Containing Side Chains and Carboxyl Group-Containing Side Chains (Sugar-PEG-A/C)

The PEG-A/C from (2) above and a sugar lactone are dissolved in dry DMF and reacted at 60-80° C. for 1.5-4 hr. A PEG derivative having sugar residue-containing side chains and carboxyl group-containing side chains can be obtained by gel filtration or lyophilization of the reaction mixture, or by removing the solvent from the reaction mixture under reduced pressure. The molar ratio of the sugar lactone to the amino group in PEG-A/C may be preferably 1:1 or more.

The molecular weight of the resultant Sugar-PEG-A/C can be calculated based on the molecular weight of PEG-A/C by determining the number of the sugar side chains by suitable techniques such as NMR. Briefly, the molecular weight of Sugar-PEG-A/C can be calculated by adding [the product of the number of sugar molecules added and the molecular weight increase caused by addition of one sugar molecule] to [the molecular weight of PEG-A/C].

Alternatively, the molecular weight of Sugar-PEG-A/C can be estimated by conventional methods using GPC with an appropriate solvent.

Salts of Sugar-PEG-A/C may be prepared as described below.

(4) Preparation of Salts of Sugar-PEG-A/C

The Sugar-PEG-A/C obtained in (3) above is dissolved in water and neutralized with an aqueous dilute NaOH or KOH solution until the pH reaches 8-11. The resultant solution is lyophilized, or the solvent is removed therefrom under reduced pressure.

(5) Preparation of Graft Copolymers

Graft copolymers can be synthesized by linking, for example, a commercial polyethylene glycol having a reactive functional group (amino group or carboxyl group) introduced at one terminal end, to the functional group of a backbone polymer using dicyclohexylcarbodiimide or the like.

1-2 Preparation of Copolymers having Sugar Residue-Containing Side Chains and Carboxyl Group-Containing Side Chains (2nd Method)

(1) Preparation of Copolymers of Allylglycidyl Ether and Ethylene Oxide

Copolymers of allylglycidyl ether and ethylene oxide are prepared in the same manner as described in (1) in Section 1-1 above.

(2) Preparation of PEG Derivatives having Pendant Carboxyl Groups (PEG-C)

The copolymer of allylglycidyl ether and ethylene oxide obtained in (1) in Section 1-1 above is dissolved in methanol, added dropwise with stirring to a mercapto-fatty acid solution in methanol, and reacted at 20-60° C. for 8-72 hr. After dilution with water, the reaction mixture is purified by gel filtration and then lyophilized to thereby obtain a PEG derivative having pendant carboxyl groups (PEG-C).

The molecular weight of the resultant PEG-C can be calculated based on the molecular weight of the copolymer of allylglycidyl ether and ethylene oxide from (1) above. Briefly, the molecular weight of PEG-C can be calculated by adding [the product of the molecular weight of the added mercapto-fatty acid and the number of the molecules added] to the molecular weight of the copolymer of allylglycidyl ether and ethylene oxide.

(3) Preparation of Polyethylene Glycol Derivatives having Sugar Residue-Containing Side Chains and Carboxyl Group-Containing Side Chains (Sugar-N-PEG-C)

The PEG derivative (PEG-C) and a sugar derivative having amino groups are dissolved in an appropriate solvent. Dicyclohexylcarbodiimide or water-soluble carbodiimide is added to the solution and reacted at a temperature ranging from room temperature to 40° C. for 18-40 hr. The reaction is terminated by optionally adding an excessive amount of sodium acetate. By purifying the reaction mixture by gel filtration, a PEG derivative having sugar side chains and carboxyl side chains can be obtained.

The molecular weight of the resultant Sugar-N-PEG-C can be calculated based on the molecular weight of the PEG derivative having pendant carboxyl groups (PEG-C). Briefly, the ratio of the sugar side chains to the carboxyl side chains in the polymer is determined from an NMR spectrum of the polymer. Then, [the product of the number of sugar molecules added and the molecular weight increase caused by addition of one sugar molecule] is added to [the molecular weight of the PEG-C].

Alternatively, the molecular weight of Sugar-N-PEG-C can be estimated by conventional methods using GPC with an appropriate solvent.

Salts of Sugar-N-PEG-C may be prepared as described below.

(4) Preparation of Salts of Sugar-N-PEG-C

Salts of Sugar-N-PEG-C are prepared in the same manner as described in (4) in Section 1-1.

(5) Preparation of Graft Copolymers

Graft copolymers can be synthesized by linking, for example, a commercial polyethylene glycol having an amino group introduced at one terminal end to the carboxyl group of a backbone polymer using dicyclohexylcarbodiimide or the like.

1-3 Preparation of Copolymers having Carboxyl Group-Containing Side Chains (1) Preparation of Copolymers of Allylglycidyl Ether and Ethylene Oxide Copolymers of allylglycidyl ether and ethylene oxide are prepared in the same manner as described in (1) in Section 1-1 above.

(2) Preparation of PEG Derivatives having Pendant Carboxyl Groups (PEG-C)

PEG derivatives having pendant carboxyl groups (PEG-C) are prepared in the same manner as described in (2) in Section 1-2 above.

The molecular weight of the resultant PEG-C can be calculated in the same manner as described in (2) in Section 1-2 above.

(3) Preparation of Salts of PEG-C

Salts of PEG-C are prepared in the same manner as described in (4) in Section 1-1 above, except that PEG-C is used instead of Sugar-PEG-A/C.

(4) Preparation of Graft Copolymers

Graft copolymers are prepared in the same manner as described in (5) in Section 1-1 above.

2. Drug Delivery Systems

Hereinbelow, an explanation is given with reference to drug delivery system for gene therapy comprising a complex of a gene and a high molecular weight chitosan as coated with Sugar-PEG-A/C or PEG-C.

Chitosan is a polysaccharide obtainable by deacetylating the acetoamide group in chitin (a polysaccharide consisting of $\beta$-1-4 linked N-acetyl-D-glucosamine) contained mainly in the shell of crustaceans such as shrimp and crab.

The high molecular weight chitosan used in the present invention may be a conventional chitosan soluble in dilute acid as long as it has an intrinsic viscosity of 1.0 dl/g or more; the source of chitosan or the degree of deacetylation is not particularly limited. If a low molecular weight chitosan whose intrinsic viscosity is lower than the above-mentioned value is used, a problem of remarkably decreased gene transfer ratios will occur.

The "intrinsic viscosity" used herein can be determined, for example, according to the method described in Japanese Unexamined Patent Publication No. 1-185301. Briefly, chitosan is dissolved in water using acetic acid in an amount equal to the amount of chitosan. The solution is mixed with an equal amount of 0.4 N acetic acid +0.2 N sodium acetate to prepare a sample solution for measurement. For dilution, 0.2 acetic acid +0.1 N sodium acetate is used. The value obtained by measurement at 30° C. with an Ubbelohde viscometer is the intrinsic viscosity.

In the present invention, it is preferable to use as the gene a plasmid (a recombinant vector) in which the DNA to be transferred is liked downstream of the promoter of the expression vector.

The gene-chitosan complex can be formed by mixing a gene solution and a chitosan solution at 0-50° C. for 10 min to 24 hr, preferably at 20-30° C. for 1-4 hr. The mixing ratio of gene to chitosan [one base of gene (e.g. plasmid): glucosamine units in chitosan] is preferably from 1:1 to 1:20, more preferably from 1:2 to 1:10. With respect to solvents for the gene and the chitosan, sterilized ultra-pure water, buffers, etc. may preferably be used. As to the solvent for plasmid solution, it is preferable to adjust its pH at 5.5-7.5.

For coating the gene-chitosan complex with Sugar-PEG-A/C or PEG-C, a Sugar-PEG-A/C or PEG-C solution is mixed with a solution of the gene-chitosan complex at 0-50° C. for 5 min to 24 hr, preferably at 20-30° C. for 10-60 min, so that an intend cation:anion ratio (charge ratio of the cation in chitosan to the anion in Sugar-PEG-A/C or PEG-C) is achieved. The cation:anion ratio may be in the range from 1:0.01 to 1:20, preferably from 1:0.1 to 1:16, and more preferably 1:0.2 to 1:10.

The cation:anion ratio can be calculated by the following formula.

[(Weight of chitosan/Mean molecular weight per repeat unit of chitosan)×(degree of deacetylation)]:[(Weight of Sugar-PEG-A/C or PEG-C)/(Molecular weight of polymer/Number of carboxyl groups per polymer molecule)]

The solvent for the Sugar-PEG-A/C or PEG-C solution may be water or a buffer, preferably a phosphate buffer.

In preferred embodiments of the present invention, the Sugar-PEG-A/C- or PEG-C-coated gene-chitosan complex prepared under the above-mentioned conditions is added as it is to a cell of interest in culture, and left stationary at the cultivation temperature of the cell for 1-12 hr to thereby achieve sufficient contact between the complex and cells. Then, the medium is exchanged with one supplemented with a serum, and cells are cultured for another 4-48 hr to thereby transfer the gene into cells. It is possible to increase the gene expression ratio by adding a serum to the medium.

The serum component used in the present invention may be any serum suitable for cell culture. For example, fetal bovine serum (FBS) or the like is preferably used. The amount of serum added to the medium is preferably 0.1-50% by weight, and more preferably 2-20% by weight.

By changing the type of the sugar used in the copolymer of the present invention, it is possible to design a number of carriers that deliver drugs (such as therapeutic genes) to various target tissues in the body. For example, it is known that pullulan has a property of targeting to brain tumor (Drug Delivery System, Vol. 5, No. 4, 1990, pp. 261-265); that lactose has affinity for many types of cancer cells (Biol. Cell, Vol. 47, 1983, pp. 95-110); that galactose and lactose have particularly high affinity for hepatoma (J. Biol. Chem., Vol. 256, 1981, pp. 8878-8881); melanoma also recognizes maltose (Naturwissenschaften Vol. 74, 1987, S. 37); and that immunocytes such as macrophage recognize mannose (Prog. Lipid. Res., Vol. 31, 1992, pp. 345-372). These pieces of information can be utilized in designing carriers for drug delivery systems and carriers for gene transfer.

Furthermore, the carrier for drug delivery systems of the present invention may also comprise spermine, peptides, cationic lipids, cationic cholesterol derivatives, folic acid, etc. in addition to polycations such as the above-described high molecular weight chitosan.

The carrier for gene transfer of the present invention may also comprise spermine, peptides, cationic lipids, cationic cholesterol derivatives, folic acid, etc. in addition to polycations such as the above-described high molecular weight chitosan.

Using the copolymer of the present invention, it has become possible to achieve gene delivery that results in higher gene expression as compared to conventional gene-chitosan complexes and that yet is cell specific. Also, by using the copolymer of the present invention, it is possible to inhibit the aggregation of gene-chitosan complexes in solutions and body fluids such as blood, and to increase the water-solubility of formulations of such complexes.

Since the drug delivery system of the present invention is a technology applicable to not only genes but also a number of nucleic acid derivatives such as antisense nucleic acid or ribozyme, this technology is expected to be utilized not only in the field of gene therapy but also in the field of biotechnology.

EXAMPLES

Hereinbelow, the present invention will be described in more detail with reference to the following Examples. These Examples are provided by way of illustration and should not be considered as limiting the present invention.

Example 1

Preparation of PEG Derivatives having Sugar Residue-Containing Side Chains and Carboxyl Group-Containing Side Chains (Mal-PEG-A/C and Lac-PEG-A/C)

Figure 4:
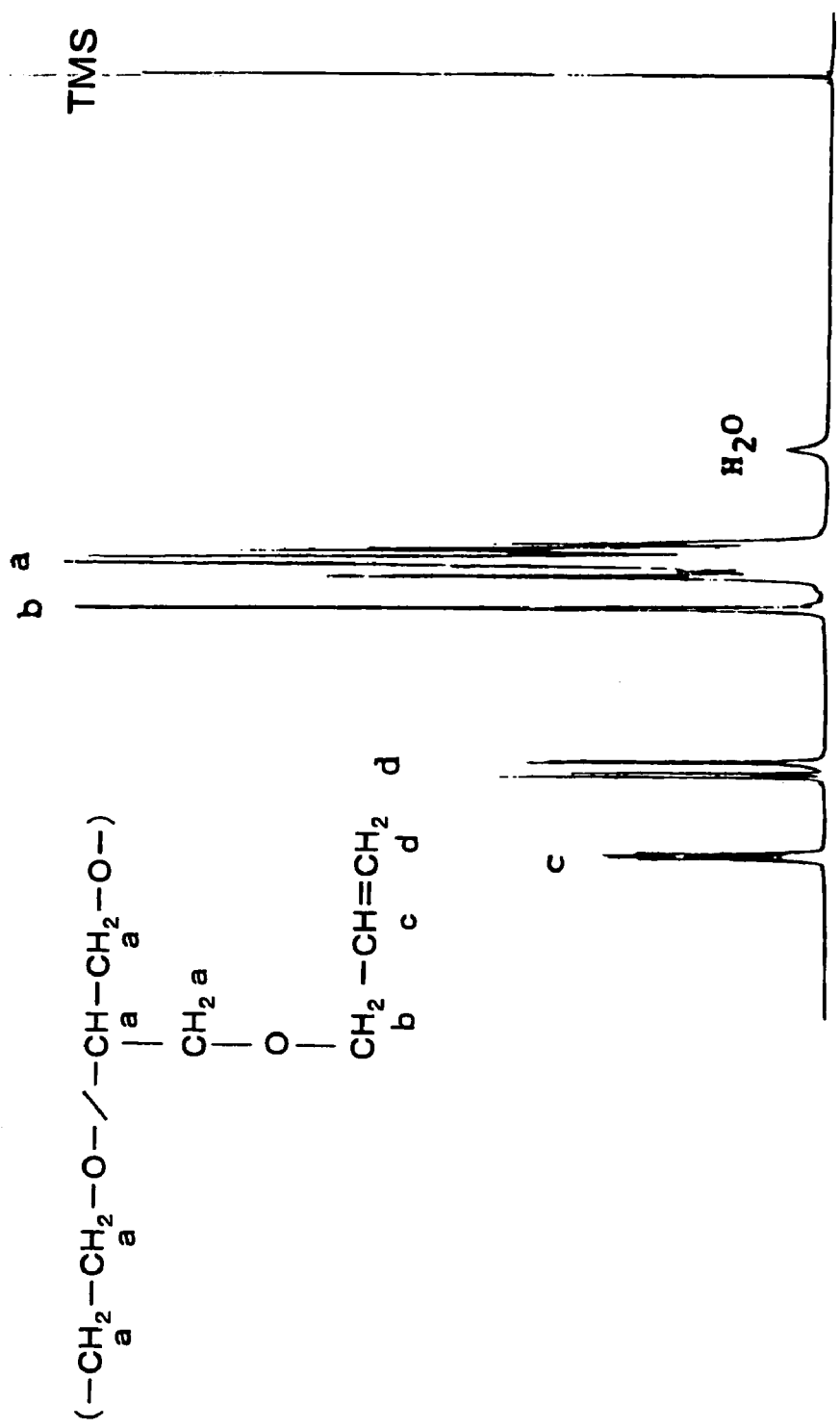
FIG. 4 is an NMR spectrum of a copolymer of allylglycidyl ether and ethylene oxide.

Diethylene glycol (56 g) and potassium hydroxide (1.2 g) were placed in a reactor and dehydrated at 85° C. for 1 hr at about 50 mmHg under a nitrogen atmosphere. Then, a mixture of allylglycidyl ether (AGE) and ethylene oxide (EO) (molar ratio 15:85) was added dropwise at 100-120° C. at a rate of about 400 g/h. The molecular weight of the resulting polymer is controlled by the amounts of monomers added. Immediately after adding allylglycidyl ether (AGE) and ethylene oxide (EO) in a total amount of 3000 g, the unreacted monomers were removed under reduced pressure (200 mmHg). After neutralization with phosphoric acid, the resultant polymer was dehydrated at 100° C. for 1 hr under reduced pressure and finally filtered at 80° C. An NMR spectrum of the resultant copolymer of allylglycidyl ether and ethylene oxide is shown in FIG. 4.

Figure 5:
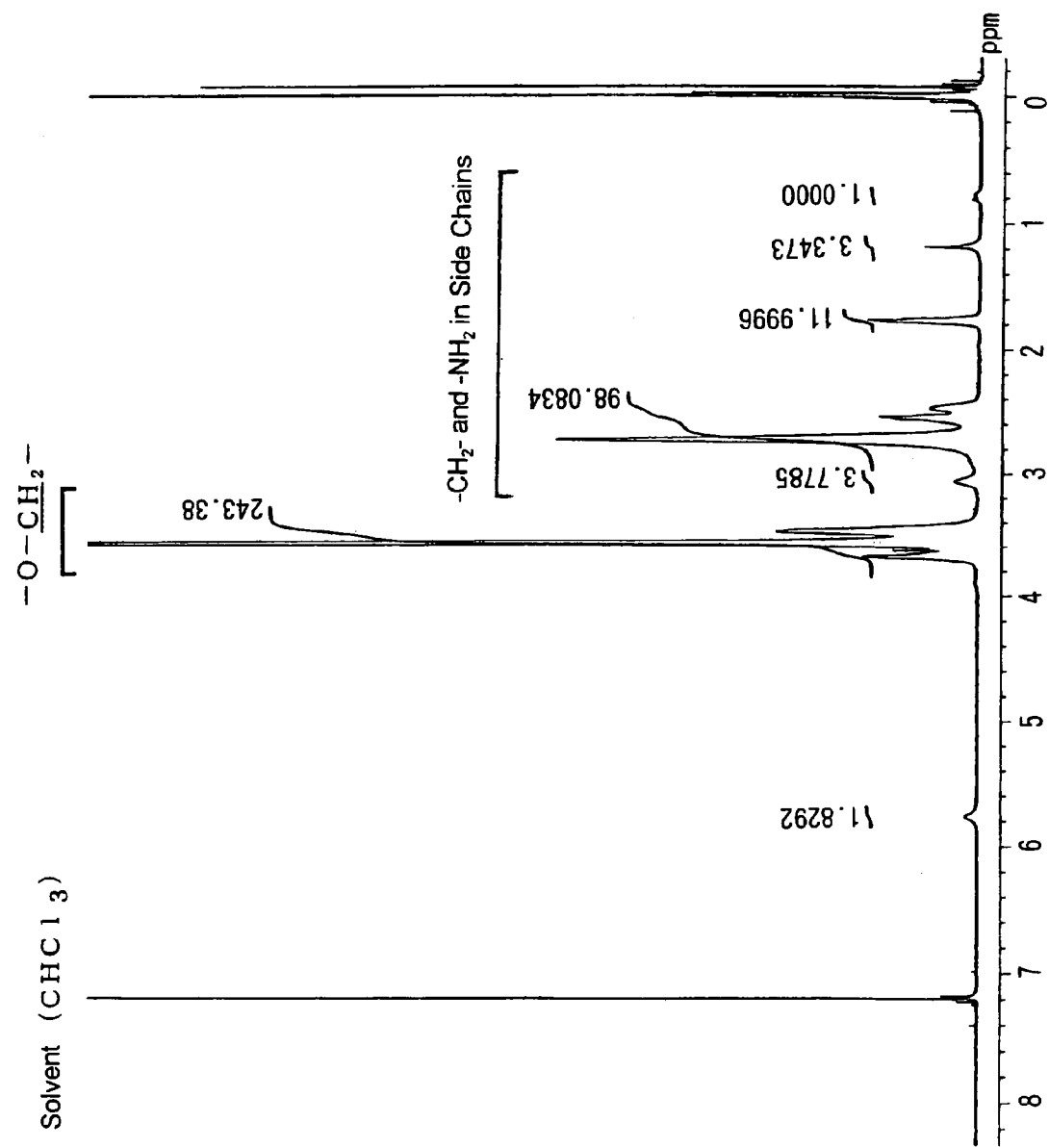
FIG. 5 is an NMR spectrum of PEG-A/C.

Two grams of the resultant copolymer of allylglycidyl ether and ethylene oxide (Mn: 7060, Mw/Mn=1.05, allylglycidyl ether:ethylene oxide=13.4:86.6) was dissolved in 4 ml of methanol and added dropwise with stirring to a mixture of aminoethanethiol (1 g) (Kanto Kagaku) and mercaptopropionic acid (3 g) (Wako Purechemical) pre-dissolved in 6 ml of methanol, and reacted at 30° C. for 50 hr. After dialysis against flowing water for 3 days and against pure water for 1 day, the reaction mixture was lyophilized to thereby obtain a PEG derivative having both pendant amino groups and pendant carboxyl groups (PEG-A/C). Yield: 1.1 g. The ratio of amino groups to carboxyl groups in the polymer calculated from an NMR spectrum of the product acetylated was 29:71. An NMR spectrum of PEG-A/C is shown in FIG. 5.

Figure 6:
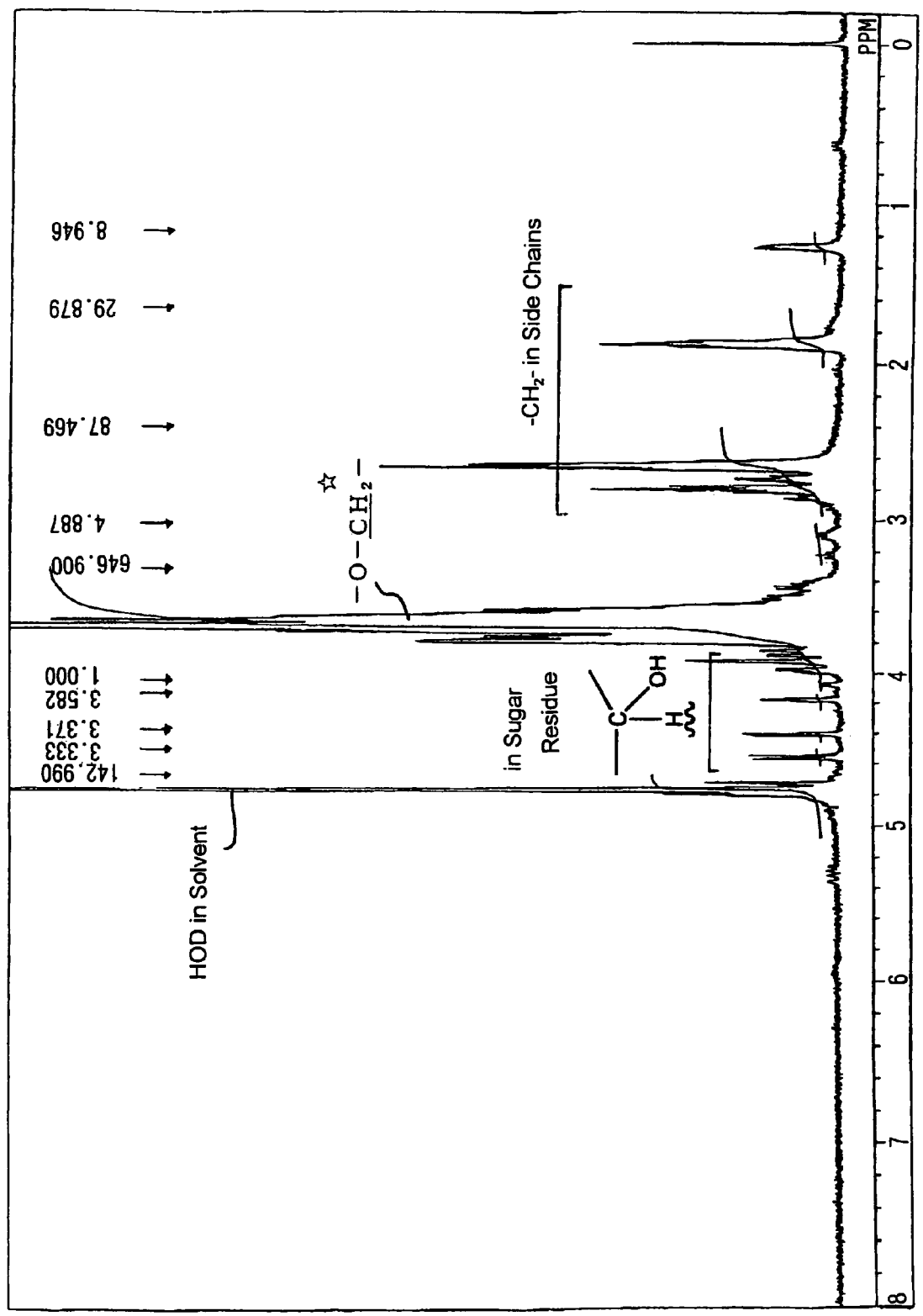
FIG. 6 is an NMR spectrum of Lac-PEG-A/C.

Subsequently, lactonolactone or maltonolactone was synthesized as described in the literature (Polymer J., Vol. 17, p. 567, 1985). Two hundred milligrams of one of these lactones and 200 mg of PEG-A/C were dissolved in 3 ml of dry DMF and reacted at 70° C. for 2.5 hr. After gel filtration, the resultant reaction mixture was lyophilized to thereby obtain a PEG derivative having both sugar residue-containing side chains and carboxyl group-containing side chains. Yield: 146-152 mg. Based on an NMR spectrum of the resultant polymer, it was confirmed that the polymer was a derivative in which every amino group had a sugar chain linked thereto (Lac-PEG-A/C or Mal-PEG-A/C). Molecular weight: 10450; Number of sugar chains per polymer molecule: 5.1; Number of COOH groups per polymer molecule: 12.6. NMR spectra of Lac-PEG-A/C and Mal-PEG-A/C are shown in FIG. 6 and 7, respectively.

The molecular weight of the copolymer of allylglycidyl ether and ethylene oxide was determined by the hydroxyl titration method (JIS K-1557 6.4 (1970)). The polymer composition was determined by the double-bond titration method (JIS K-1557 6.7 (1970)). The molecular weight distribution was examined by GPC (solvent: THF). All the molecular weights of subsequent products were calculated based on the thus determined molecular weight.

Reference Example 1

Preparation of PEG Derivative having Pendant Carboxyl Groups (PEG-C9000)

Two grams of a copolymer of allylglycidyl ether and ethylene oxide (Mn=3260; Mw/Mn=1.05; 8.28 C=C groups/polymer molecule) dissolved in 4 ml of methanol was added dropwise at room temperature to 4 g of 3-mercaptopropionic acid dissolved in 2 ml of methanol. After the mixture was left at 40° C. for 70 hr, re-precipitation was repeated with a methanol/ether system, followed by gel filtration (Sephadex G-50). Thus, the polymer was purified. Finally, the polymer was lyophilized to obtain syrup-like PEG-C9000 (2.3 g). An NMR spectrum of PEG-C9000 is shown in FIG. 8.

Example 2

Preparation of Chitosan

Chitosan hydroacetate (Yaizu Suisan) was placed in a bottle, and 12 N HCl was added with stirring with a magnetic stirrer until the solution became clear. The resultant powder was lyophilized. The resultant chitosan hydrochloride had mean molecular weights of 40, 84 and 110 kDa. The degree of deacetylation was about 85%.

Example 3

Gene Expression in Chitosan/PEG Derivative/Plasmid Complexes

Complexes consisting of three components, a gene, chitosan and a PEG derivative, were prepared. These complexes were interacted with mouse melanoma cell B 16, followed by confirmation of the expression of luciferase gene.

Operation Procedures (1) The day before transfer of the complex, B16 cells (JCRB Cell Bank) were plated in 24-well multiplates at $5 \times 10^4$ cells/well and incubated for 24 hr.
(2) The pH of PBS(−) was adjusted to 6.5 with 1N HCl.
(3) Luciferase plasmid (7.5 μl) (Promega; 1 mg/ml) was diluted with the adjusted PBS(−) (135 μl) and left at room temperature for 15 min.
(4) To the plasmid solution obtained in (3) above, 7.5 μl of an aqueous solution of the chitosan hydrochloride (mean molecular weight: 40 kDa) prepared in Example 2 (2.95 mg/ml) was added. After pipetting several times, the resultant solution was left stationary at room temperature for 15 min.
(5) To the solution obtained in (4) above, solutions of the PEG derivatives prepared in Reference Example 1 (PEG-C9000) and Example 1 (Mal-PEG-A/C and Lac-PEG-A/C) [40 mg of each PEG derivative was dissolved in 1 ml of MilliQ or PBS(−)] were added separately to give specific cation:anion ratios, and then left stationary for 15 min. The cation:anion ratios used here were 1:0.5, 1:1, 1:2, and 1:4. Specifically, the cation:anion ratio means the molar ratio between the electric charge on chitosan and the electric charge on the PEG derivative. The cation:anion ratio was calculated by the following formula. [(Weight of chitosan/Mean molecular weight per repeat unit of chitosan)×(degree of deacetylation)]:[(Weight of Sugar-PEG-A/C or PEG-C9000)/(Molecular weight of polymer/Number of carboxyl groups per polymer molecule)]
(6) While the above solution was left stationary, a medium [containing 10 mM PIPES (Sigma) or MOPS (Sigma) and 10% serum (Sigma)] whose pH had been adjusted to 6.5 with 1N HCl was prepared and dispensed into the plates at 500 μl /well.
(7) The thus prepared complex solution was pipetted sufficiently, and then added to each well of the plates.
(8) The plates were incubated at 37° C. under 5% $CO_2$-95% air for 4 hr.
(9) The complex-containing medium was removed. Cell surfaces were washed with PBS(−) two or three times. Then, a fresh medium was added.
(10) After a 24-hr incubation, cell surfaces were washed with PBS(−) three times. Then, a cell lysis solution (Promega; a reagent contained in Luciferase Assay Kit) was added to each well at 100 μl /well. After the plates were left stationary for about 15 min, cells were scraped off with a cell scraper and recovered into Eppendorf tubes.
(11) After centrifugation (12000 rpm, 1 min), luciferase assay (using Luciferase Assay Kit; Promega) was carried out with the resultant supernatant.

For protein assay, the cell lysate was used without any processing. Protein assay was carried out using Protein Assay Kit from Bio-Rad.

For the purpose of comparison, gene expression in complexes without PEG derivatives was also examined.

Results

Figure 1:
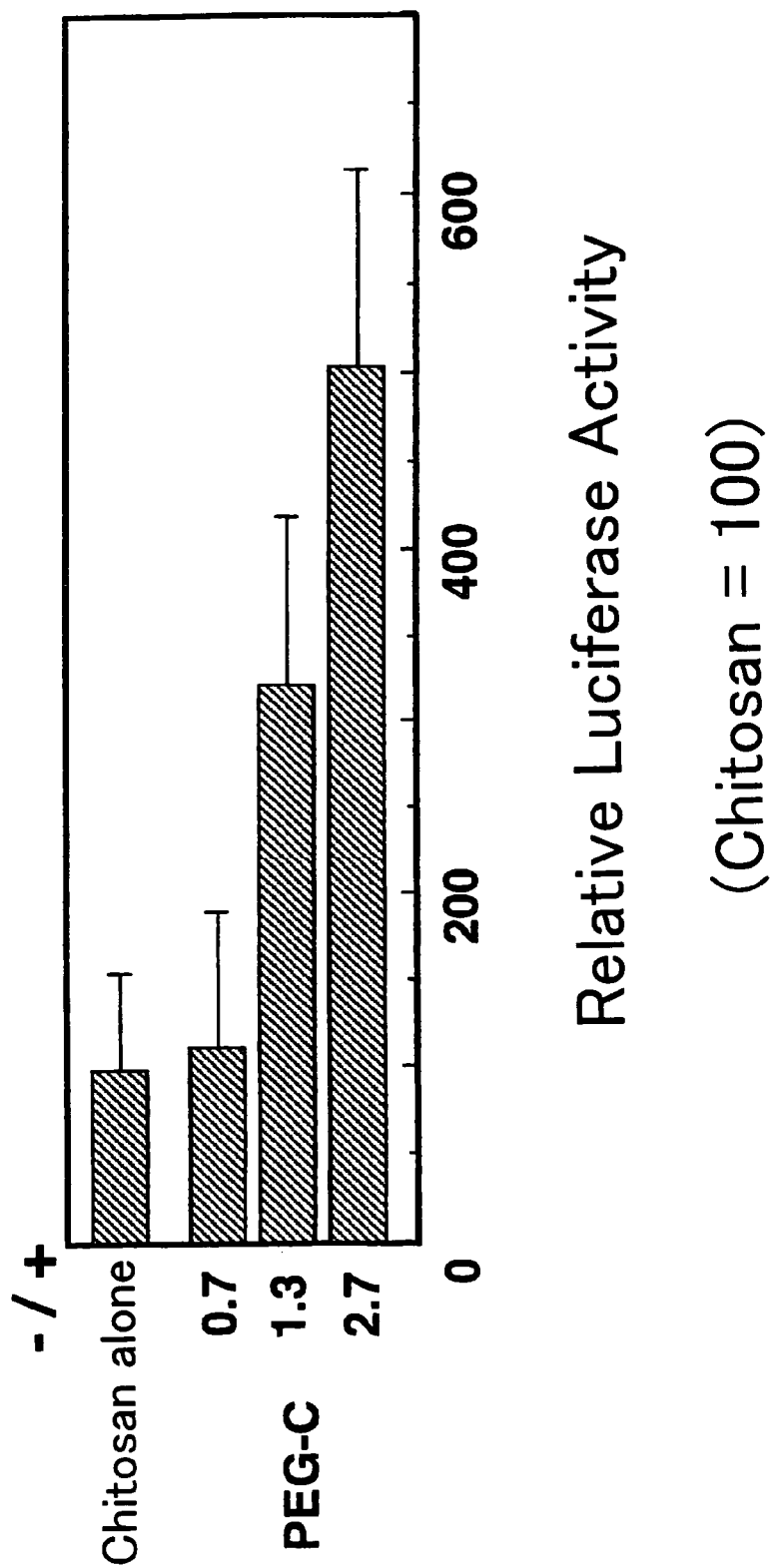
FIG. 1 is a graph showing the effect of anion/cation ratios in PEG-C.
Figure 2:
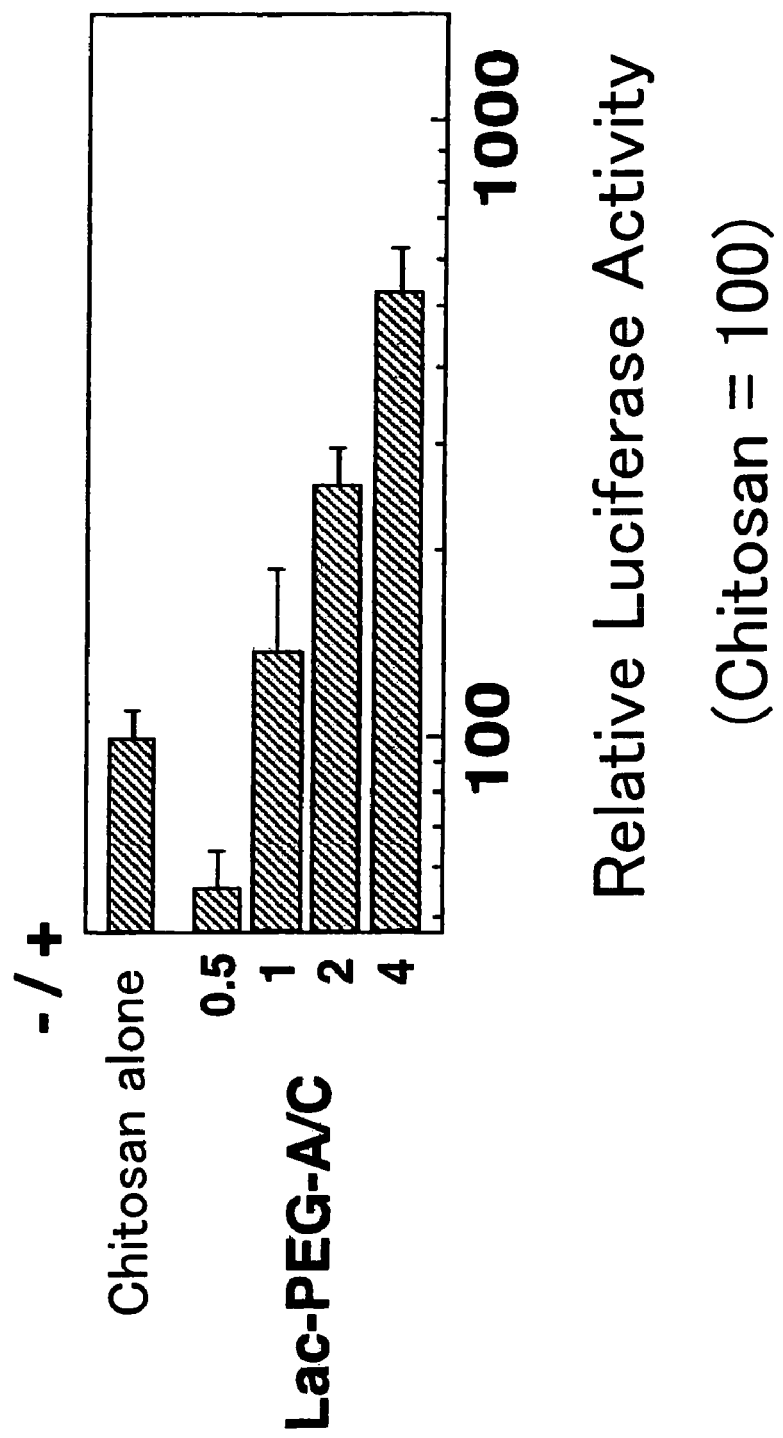
FIG. 2 is a graph showing the effect of anion/cation ratios in Lac-PEG-A/C.
Figure 3:
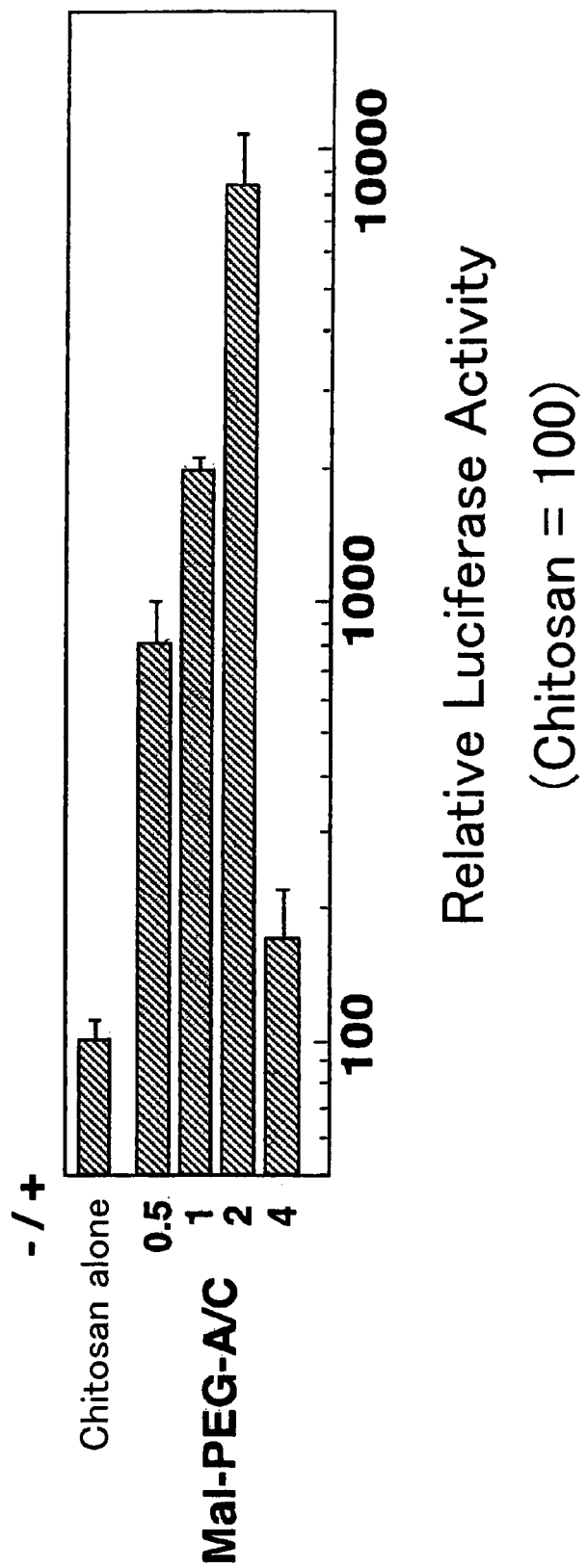
FIG. 3 is a graph showing the effect of anion/cation ratios in Mal-PEG-A/C.

The results are shown in FIGS. 1 to 3. The values of −/+ appearing in these Figures represent anion/cation ratios. Specifically, those values are molar ratios of the electric charge on PEG derivative to the electric charge on chitosan.

FIG. 1 shows that PEG-C9000 largely improved gene expression in an anion/cation ratio-dependent manner.

FIG. 2 shows the results for Lac-PEG-A/C. The expression activity was highest when the anion/cation ratio was 4; gene expression increased almost 12-fold as compared to the expression in the complex to which Lac-PEG-A/C was not added.

FIG. 3 shows the results for Mal-PEG-A/C. The expression activity was highest when the anion/cation ratio was 2; gene expression increased almost 85-fold as compared to the expression in the complex to which Mal-PEG-A/C was not added.

Example 4

Gene Expression in Polyethyleneimine/PEG Derivative/Plasmid Complexes

Complexes consisting of three components, a gene, polyethyleneimine and a PEG derivative, were prepared. These complexes were interacted with human hepatoma cell HepG2, followed by confirmation of the expression of luciferase gene.

Operation Procedures (1) The day before transfer of the complex, HepG2 cells were plated in 96-well multiplates at $1 \times 10^4$ cells/well and incubated for 24 hr.
(2) Luciferase plasmid (100 ng) was dissolved in 45 μl of DMEM medium (−). To the solution, 5 μl of linear polyethyleneimine (Polyscience; mean molecular weight: 25 kDa) dissolved in DMEM medium (−) was added and left stationary at 37° C. for 30 min. The concentration of the polyethyleneimine solution was adjusted to give an anion/cation ratio of 1:4.
(3) To the solution obtained in (2), solutions of the PEG derivatives prepared Example 1 (Mal-PEG-A/C and Lac-PEG-A/C) were added separately to give specific cation:anion ratios, and then left stationary at 37° C. for 30 min. Specifically, the cation:anion ratio means the molar ratio between the electric charge on polyethyleneimine and the electric charge on the PEG derivative.
(4) To each well of the plates, 55 μl of the complex solution thus prepared was added. Further, a chloroquine solution in DMEM was added to give a final chloroquine concentration of $2 \times 10^{-4}$ M.
(5) The plates were incubated at 37° C. under 5% $CO_2$-95% air for 10 hr.
(6) The complex-containing medium was removed. Cell surfaces were washed with PBS(−) two or three times. Then, a fresh medium was added.

(7) After a 40-hr incubation, cell surfaces were washed with PBS(−) three times. Then, cells were lysed with 1% by weight of Triton X-100 solution and subjected to luciferase assay.

Results

The results are shown in FIGS. 9 and 10. The values of −/+ appearing in these Figures represent anion/cation ratios. Specifically, those values are molar ratios of the electric charge on PEG derivative to the electric charge on polyethyleneimine. The term "protein" appearing in FIGS. 9 and 10 means all the proteins contained in the cell. The "Relative Luciferase Activity per mg of Protein" is a value that represents how much of the total protein produced by the cell is attributable to luciferase gene.

FIG. 9 shows the results for Lac-PEG-A/C. The expression activity was highest when the anion/cation ratio was 4; gene expression increased about 3-fold as compared to the expression in the complex to which Lac-PEG-A/C was not added.

FIG. 10 shows the results for Mal-PEG-A/C. The expression activity was highest when the anion/cation ratio was 8; gene expression increased about 2-fold as compared to the expression in the complex to which Mal-PEG-A/C was not added.

Example 5

Preparation of PEG Derivatives having Sugar Side Chains and Carboxyl Side Chains (Gul-N-PEG-C, Gal-N-PEG-C and Man-N-PEG-C) as Prepared Using Amino Group-Containing Sugar Derivatives One hundred milligrams of a PEG derivative having pendant carboxyl groups (PEG-C9000) (MW: 8940; number of COOH per polymer molecule: 17.7) that was synthesized in the same manner as in Reference Example 1 and 15 mg of p-aminophenyl glucoside were dissolved in 1 ml of pure water, followed by addition of 40 mg of water-soluble carbodiimide. Two milliliters of pure water was further added to the solution, which was then allowed to react at room temperature for 24 hr. The reaction was terminated by adding 150 mg of sodium acetate. The resultant reaction mixture was subjected to gel-filtration with Sephacryl S-200 and then lyophilized. The resultant syrup was re-dissolved in pure water, ion-exchanged using Amberlite B-120 and lyophilized, to thereby obtain a PEG derivative having glucoside side chains and carboxyl side chains. Yield: 45 mg. The ratio of the sugar side chains to the carboxyl side chains in the polymer as calculated from the NMR spectrum was 19:81.

Likewise, a PEG derivative having galactoside side chains and carboxyl side chains was obtained using p-aminophenyl galactoside instead of p-aminophenyl glucoside. Yield: 14 mg. The ratio of the sugar side chains to the carboxyl side chains in the polymer as calculated from the NMR spectrum was 26:74.

Likewise, a PEG derivative having mannoside side chains and carboxyl side chains was obtained using p-aminophenyl mannoside instead of p-aminophenyl glucoside. Yield: 52 mg. The ratio of the sugar side chains to the carboxyl side chains in the polymer as calculated from the NMR spectrum was 23:77.

NMR spectra of the PEG derivatives having glucoside side chains and carboxyl side chains are shown in FIGS. 11 to 13.

FIGS. 11, 12 and 13 show NMR spectra of Gul-N-PEG-C, Gal-N-PEG-C and Man-N-PEG-C, respectively.

Example 6

Preparation of lactose-modified PEG-C (Lac-PEG-C)

Thirty milligrams of 2-azido-ethyl-O-(O-β-D-galactopyranosyl-(1→4)-β-D-glucopyranoside) and a stirrer were placed in a three-necked flask and dried in a vaccum for 30 minutes, and then the air in the flask was replaced with $N_2$. While 95.7 mg (corresponding to 5 equivalents of the raw material) of triphenylphosphine (Wako Purechemical) was dissolved in 5 mL of dimethylformamido (DMF, Wako Purechemical), followed by addition of 1 mL of water. The resultant solution was poured into the three-necked flask by using a syringe. The resultant mixture was reacted at 50° C. for 3.5 hr to synthesize 2-amino-ethyl-O-(O-β-D-galactopyranosyl-(1→4)-β-D-glucopyranoside) (Lac-$C_2H_4$-$NH_2$). After the confirmation of the termination of reaction by thin-layer chromatography (solvent: chloroform/methanol=3/2, orcinol-staining) and Kayser test, the reaction mixture was concentrated by an evaporator.

To use in the next condensation reaction with PEG-C, the reaction mixture was washed with water, then filtered to remove triphenylphosphine which is impurity.

The synthesized compound was identified by ESI-MS(m/z=386.25 [M+H]+, ca.=386.3) and $^1$H-NMR. (FIG. 14)

Subsequently, the obtained Lac-$C_2H_4$-$NH_2$ was dissolved in 4 ml of Milli-Q, and 30.0 mg of a PEG derivative having pendant carboxyl groups (PEG-C9000) (MW: 8940; the number of COOH per polymer molecule: 17.7) that was synthesized in the same manner as in Reference Example 1 and 861 μL of the Lac-$C_2H_4$-$NH_2$ solution were mixed, followed by addition of 30.5 mg (about 0.1 M) of 1-[3-(dimethylamino)propyl]-3-ethyl carbodiimide hydrochloride (EDC) (Aldrich). The mixture was then stirred at room temperature for 24 hr. The termination of reaction was confirmed by thin-layer chromatography (solvent: water/n-butanol/acetic acid=3/2/2, orcinol-staining), and the reaction mixture was then concentrated by an evaporator.

The product was purified by gel filtration (carrier: Sephadex G-50 Fine (Amersham), column: Φ15 mm×70 mm, development solvent:water) and cation exchange. After concentration by an evaporator, the purified product was lyophilized.

The product was identified by $^1$H-NMR (FIG. 15).

The number of modifying sugar (Rn) was calculated from the ratio of (a) described in the NMR chart to the integration value of ①+❶Rn, the number of sugars which are present in Lac PEG-C, can be calculated in the following manner.

(the integration value of ①+❶):(the integration value of (a))=(the number of protons of ①+ ❶):(the number of protons of (a)) (the integration value of (a))=(the integration value of (②~⑥)', ❷~❻, a, f, g)−(the integration value of ②~⑥)', ❷~❻, f, g)=201.49−18=183.49, (①+the number of protons of ①+ ❶=2R$_n$, (the number of protons of (a))=(4×114.3)+(7×17.7)
=581, thus, R$_n$=3.2

Accordingly, it was considered that 3 Lac molecules per PEG-C molecule were added.

Example 7

Gene Expression in Chitosan/PEG Derivative/Plasmid Complexes

Complexes consisting of three components, a gene, chitosan and a PEG derivative, were prepared. These complexes were interacted with human hepatoma cell HyH-7, followed by confirmation of the expression of luciferase gene. It is known that human hepatoma cell HyH-7 having an asialoglycoprotein receptor takes up the complex including β-Gal by receptor-mediated endocytosis.

Operation Procedures
(1) The day before transfer of the complex, HyH-7 cells were plated in 24-well multiplates at 5×10$^4$cells/well and incubated for 24 hr.
(2) The pH of PBS(−) was adjusted to 6.5 with 1N HCl.
(3) Luciferase plasmid (7.5 μl) (Promega; 1 mg/ml) was diluted with the adjusted PBS(−) (135 μl) and left at room temperature for 15 min.
(4) To the plasmid solution obtained in (3) above, 7.5 μl of an aqueous solution of the chitosan hydrochloride (mean molecular weight: 40 kDa) prepared in Example 2 (2.95 mg/ml) was added. After pipetting several times, the resultant solution was left stationary at room temperature for 15 min.
(5) To the solution obtained in (4) above, solutions of the PEG derivatives prepared in Example 6 (Lac-PEG-C) [40 mg of each PEG derivative was dissolved in 1 ml of MilliQ or PBS(−)] were added separately to give specific cation:anion ratios, and then left stationary for 15 min. The cation:anion ratios used here were 1:0.7, 1:1.7, 1:3.3, and 1:5. Specifically, the cation:anion ratio means the molar ratio between the electric charge on chitosan and the electric charge on the PEG derivative. The cation:anion ratio was calculated by the following formula.

[(Weight of chitosan/Mean molecular weight per repeat unit of chitosan)×(degree of deacetylation)]:[(Weight of Lac-PEG-C)/(Molecular weight of polymer/Number of carboxyl groups per polymer molecule)]

(6) While the above solution was left stationary, a medium [containing 10 mM PIPES (Sigma) or MOPS (Sigma) and 10% serum (Sigma)] whose pH had been adjusted to 6.5 with 1N HCl was prepared and dispensed into the plates at 500 μl /well.
(7) The thus prepared complex solution was pipetted sufficiently, and then added to 3 wells of the plates.
(8) The plates were incubated at 37° C. under 5% CO$_2$-95% air for 4 hr.
(9) The complex-containing medium was removed. Cell surfaces were washed with PBS(−) two or three times. Then, a fresh medium was added.
(10) After a 24-hr incubation, cell surfaces were washed with PBS(−) three times. Then, a cell lysis solution (Promega; a reagent contained in Luciferase Assay Kit) was added to each well at 100 μl /well. After the plates were left stationary for about 15 min, cells were scraped off with a cell scraper and recovered into Eppendorf tubes.
(11) After centrifugation (12000 rpm, 1 min), luciferase assay (using Luciferase Assay Kit; Promega) was carried out with the resultant supernatant.

For protein assay, the cell lysate was used without any processing. Protein assay was carried out using Protein Assay Kit from Bio-Rad.

For the purpose of comparison, gene expression in complexes without PEG derivatives was also examined.

FIG. 16 shows the results for Lac-PEG-C. The expression activity was highest when the anion/cation ratio was 1.7; gene expression increased almost 3.5-fold as compared to the expression in the complex to which Lac-PEG-C was not added.

All publications, patents and patent applications cited herein are incorporated herein by reference in their entity.

According to the present invention, it is possible to achieve gene delivery that results in higher gene expression activity as compared to the gene expression achieved with conventional gene-chitosan complexes, and which yet is cell specific.

Also, according to the present invention, it is possible to achieve gene delivery that results in higher gene expression activity as compared to the gene expression achieved with conventional gene-polyethyleneimine complexes, and which yet is cell specific.

What is claimed is:

1. A copolymer, or a salt thereof, with a molecular weight of 1,000-200,000 comprising structural units represented by the following formulas (I), (II), and (III):

where $R^1$ in formula (I) is a group represented by the following formula (C) or (D), and $R^2$ in formula (II) is a group represented by the following formula (B), (D) or (E):

$$*-(CH_2)_n-S-(CH_2)_p-(CO)_t-NH-X_u- \quad (B)$$

where X is hydrocarbon group, n is an integer from 2 to 8; p is an integer from 1 to 8; t is an integer 0 or 1; u is an integer 0 or 1; and * may be positioned on the ethylene oxide side or on the opposite side (C)  $*-(CH_2)_m-S-(CH_2)_p-$ where m is an integer from 2 to 8; p is an integer from 1 to 8; and * may be positioned on the ethylene oxide side or on the opposite side

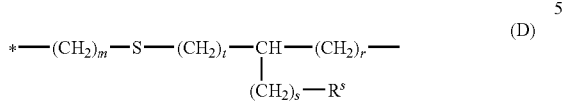 (D)

where m is an integer from 2 to 8; r is an integer from 0 to 7; s is an integer from 0 to 7; t is an integer from 0 to 4; $R^S$ an amino group, carboxyl group or sugar residue; and * may be positioned on the ethylene oxide side or on the opposite side

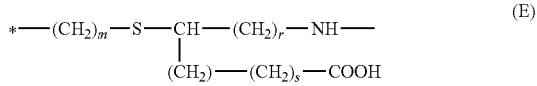 (E)

where m is an integer from 2 to 8; r is an integer from 0 to 7; s is an integer from 0 to 7; and * may be positioned on the ethylene oxide side or on the opposite side;

$R^3$ in general formula (II) is a sugar residue; and the respective mole percents of units (I), (II) and (III) are (I)=1-98, (II)=1-98 and (III)=1-98.

2. The copolymer, or a salt thereof, according to claim 1, wherein $R^3$ is a sugar residue including at least one sugar unit selected from the group consisting of galactose, maltose, glucose, N-acetylglucosamine, N-acetylgalactosamine, fucose, sialic acid, mannose, lactose, cellobiose, and maltotriose.

3. The copolymer, or a salt thereof, according to claim 1, wherein the group $R^3$ includes at least one sugar lactone selected from the group consisting of lactonolactone, maltonolactone, gluconolactone, maltotrionolactone, cellobionolactone, galactonolactone, N-acetylglucosaminolactone, N-acetylgalactosaminolactone, sialolactone, and mannolactone.

* * * * *